United States Patent
Wu et al.

(10) Patent No.: US 10,858,447 B2
(45) Date of Patent: Dec. 8, 2020

(54) ANTI-PCSK9 ANTIBODY AND USE THEREOF

(71) Applicants: JUNSHI BIOSCIENCES CO., LTD., Shanghai (CN); JUNGMENG BIOSCIENCES CO., LTD., Suzhou, Jiangsu (CN)

(72) Inventors: Hai Wu, Shanghai (CN); Bo Chen, Shanghai (CN); Hui Feng, Shanghai (CN); Sheng Yao, Shanghai (CN); Jian Yao, Shanghai (CN); Hongchuan Liu, Shanghai (CN); Libo Zhang, Shanghai (CN); Jing Zhang, Shanghai (CN); Dan Meng, Shanghai (CN)

(73) Assignees: Junshi Biosciences Co., Ltd., Shanghai (CN); Junmeng Biosciences Co., Ltd., Jiangsu (CN)

( * ) Notice: Subject to any disclaimer, the term of this patent is extended or adjusted under 35 U.S.C. 154(b) by 0 days.

(21) Appl. No.: 15/779,438

(22) PCT Filed: Nov. 24, 2016

(86) PCT No.: PCT/CN2016/107042
§ 371 (c)(1),
(2) Date: May 25, 2018

(87) PCT Pub. No.: WO2017/088782
PCT Pub. Date: Jun. 1, 2017

(65) Prior Publication Data
US 2019/0233540 A1  Aug. 1, 2019

(30) Foreign Application Priority Data
Nov. 27, 2015  (CN) .......................... 2015 1 0846855

(51) Int. Cl.
| | | |
|---|---|---|
| *C07K 16/40* | (2006.01) | |
| *A61P 3/06* | (2006.01) | |
| *A61K 51/00* | (2006.01) | |
| *A61K 51/10* | (2006.01) | |
| *A61K 39/395* | (2006.01) | |
| *A61K 47/68* | (2017.01) | |
| *A61K 39/00* | (2006.01) | |

(52) U.S. Cl.
CPC ............ *C07K 16/40* (2013.01); *A61K 39/395* (2013.01); *A61K 47/6871* (2017.08); *A61K 51/00* (2013.01); *A61K 51/1075* (2013.01); *A61P 3/06* (2018.01); *A61K 2039/505* (2013.01); *C07K 2317/21* (2013.01); *C07K 2317/24* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 7,300,655 B2 * | 11/2007 | Hansen | ............. | A61K 41/0095 424/130.1 |
| 9,090,679 B2 * | 7/2015 | Yokoseki | ............... | C07K 16/18 |
| 2015/0004174 A1 | 1/2015 | Wasserman et al. | | |

FOREIGN PATENT DOCUMENTS

| | | |
|---|---|---|
| CN | 101679527 A | 3/2010 |
| CN | 102459335 A | 5/2012 |
| JP | 2010523135 A | 7/2010 |
| JP | 2014516953 A | 7/2014 |
| JP | 2015530867 A | 10/2015 |
| JP | 5812418 B2 | 11/2015 |
| JP | 2015205883 A | 11/2015 |

OTHER PUBLICATIONS

Vajdos et al. (J Mol Biol. Jul. 5, 2002;320(2):415-28) (Year: 2002).*
Brown et al. (J Immunol. May 1996;156(9):3285-91)_ (Year: 1996).*
International Search Report in PCT/CN2016/107042, dated Feb. 28, 2017, 4 pages.

* cited by examiner

*Primary Examiner* — Brian Gangle
*Assistant Examiner* — Andrea K McCollum
(74) *Attorney, Agent, or Firm* — Kilpatrick Townsend & Stockton LLP

(57) ABSTRACT

The present invention provides an antibody or a functional fragment thereof that specifically binds to Proprotein convertase subtilisin/kexin type 9 (PCSK9) with high affinity, also provides a nucleic acid molecule encoding the antibody of the invention or the functional fragment thereof, for expressing an expression vector and a host cell of the antibody or the functional fragment thereof, and also provides a method for producing the antibody or the functional fragment thereof. The present invention provides that the antibody or the functional fragment thereof is used for treating diseases such as dyslipidemia.

20 Claims, 6 Drawing Sheets

Specification includes a Sequence Listing.

| | 3G12 murine-derived antibody | 3G12 chimeric antibody |
|---|---|---|
| EC50 | 78030 | 33838 |

SEQUENCE LISTING

<160> NUMBER OF SEQ ID NOS: 53

<210> SEQ ID NO 1
<211> LENGTH: 10
<212> TYPE: PRT
<213> ORGANISM: Mus musculus

<400> SEQUENCE: 1

Ala Ser Gln Asp Ile Asn Lys Tyr Ile Asp
1               5                   10

```
<210> SEQ ID NO 2
<211> LENGTH: 7
<212> TYPE: PRT
<213> ORGANISM: Mus musculus

<400> SEQUENCE: 2

Tyr Thr Ser Thr Leu Gln Pro
1               5

<210> SEQ ID NO 3
<211> LENGTH: 8
<212> TYPE: PRT
<213> ORGANISM: Mus musculus

<400> SEQUENCE: 3

Val Gln Tyr Asp Asp Leu Trp Thr
1               5

<210> SEQ ID NO 4
<211> LENGTH: 5
<212> TYPE: PRT
<213> ORGANISM: Mus musculus

<400> SEQUENCE: 4

Ser Tyr Gly Val His
1               5

<210> SEQ ID NO 5
<211> LENGTH: 16
<212> TYPE: PRT
<213> ORGANISM: Mus musculus

<400> SEQUENCE: 5

Val Ile Trp Arg Gly Gly Ser Thr Asp Tyr Asn Ala Ala Phe Met Ser
1               5                   10                  15

<210> SEQ ID NO 6
<211> LENGTH: 3
<212> TYPE: PRT
<213> ORGANISM: Mus musculus

<400> SEQUENCE: 6

His Arg Asp
1

<210> SEQ ID NO 7
<211> LENGTH: 10
<212> TYPE: PRT
<213> ORGANISM: Mus musculus

<400> SEQUENCE: 7

Ala Ser Gln Asp Ile Asn Lys Tyr Ile Asp
1               5                   10

<210> SEQ ID NO 8
<211> LENGTH: 7
<212> TYPE: PRT
<213> ORGANISM: Mus musculus

<400> SEQUENCE: 8

Tyr Ala Ser Thr Leu Gln Pro
1               5
```

```
<210> SEQ ID NO 9
<211> LENGTH: 8
<212> TYPE: PRT
<213> ORGANISM: Mus musculus

<400> SEQUENCE: 9

Leu Gln Tyr Asp Asp Leu Trp Thr
1               5

<210> SEQ ID NO 10
<211> LENGTH: 5
<212> TYPE: PRT
<213> ORGANISM: Mus musculus

<400> SEQUENCE: 10

Ser Tyr Gly Ile His
1               5

<210> SEQ ID NO 11
<211> LENGTH: 16
<212> TYPE: PRT
<213> ORGANISM: Mus musculus

<400> SEQUENCE: 11

Val Ile Trp Arg Gly Gly Ile Thr Asp Tyr Asn Ala Pro Phe Met Ser
1               5                   10                  15

<210> SEQ ID NO 12
<211> LENGTH: 3
<212> TYPE: PRT
<213> ORGANISM: Mus musculus

<400> SEQUENCE: 12

His Arg Asp
1

<210> SEQ ID NO 13
<211> LENGTH: 15
<212> TYPE: PRT
<213> ORGANISM: Mus musculus

<400> SEQUENCE: 13

Arg Ala Ser Glu Ser Val Asp Asn Tyr Gly Ile Ser Phe Met Asn
1               5                   10                  15

<210> SEQ ID NO 14
<211> LENGTH: 7
<212> TYPE: PRT
<213> ORGANISM: Mus musculus

<400> SEQUENCE: 14

Thr Thr Ser Asn Gln Gly Ser
1               5

<210> SEQ ID NO 15
<211> LENGTH: 9
<212> TYPE: PRT
<213> ORGANISM: Mus musculus

<400> SEQUENCE: 15

Gln Gln Ser Lys Glu Val Pro Tyr Thr
1               5
```

```
<210> SEQ ID NO 16
<211> LENGTH: 6
<212> TYPE: PRT
<213> ORGANISM: Mus musculus

<400> SEQUENCE: 16

Ser Asp Tyr Ala Trp Asn
1               5

<210> SEQ ID NO 17
<211> LENGTH: 16
<212> TYPE: PRT
<213> ORGANISM: Mus musculus

<400> SEQUENCE: 17

Tyr Ile Ser Tyr Ser Gly Ser Ser Ser Tyr Asn Pro Ser Leu Lys Gly
1               5                   10                  15

<210> SEQ ID NO 18
<211> LENGTH: 11
<212> TYPE: PRT
<213> ORGANISM: Mus musculus

<400> SEQUENCE: 18

Phe Tyr Tyr Arg Phe Asp Ala Tyr Phe Asp Ser
1               5                   10

<210> SEQ ID NO 19
<211> LENGTH: 15
<212> TYPE: PRT
<213> ORGANISM: Mus musculus

<400> SEQUENCE: 19

Arg Ala Ser Glu Ser Val Glu Tyr Tyr Gly Thr Ser Leu Met His
1               5                   10                  15

<210> SEQ ID NO 20
<211> LENGTH: 7
<212> TYPE: PRT
<213> ORGANISM: Mus musculus

<400> SEQUENCE: 20

Ser Gly Ser Asn Val Glu Ser
1               5

<210> SEQ ID NO 21
<211> LENGTH: 9
<212> TYPE: PRT
<213> ORGANISM: Mus musculus

<400> SEQUENCE: 21

Gln Gln Ser Arg Glu Val Pro Ser Thr
1               5

<210> SEQ ID NO 22
<211> LENGTH: 6
<212> TYPE: PRT
<213> ORGANISM: Mus musculus

<400> SEQUENCE: 22

Ser Asp Tyr Ala Trp Asn
1               5
```

<210> SEQ ID NO 23
<211> LENGTH: 16
<212> TYPE: PRT
<213> ORGANISM: Mus musculus

<400> SEQUENCE: 23

Tyr Ile Ser Tyr Ser Gly Thr Thr Asn Tyr Asn Pro Ser Leu Lys Ser
1               5                   10                  15

<210> SEQ ID NO 24
<211> LENGTH: 10
<212> TYPE: PRT
<213> ORGANISM: Mus musculus

<400> SEQUENCE: 24

Arg Glu Gly His Tyr Ser Trp Phe Pro Tyr
1               5                   10

<210> SEQ ID NO 25
<211> LENGTH: 11
<212> TYPE: PRT
<213> ORGANISM: Mus musculus

<400> SEQUENCE: 25

Arg Ala Ser Glu Asn Ile Tyr Ser Tyr Leu Ala
1               5                   10

<210> SEQ ID NO 26
<211> LENGTH: 7
<212> TYPE: PRT
<213> ORGANISM: Mus musculus

<400> SEQUENCE: 26

Asn Ala Tyr Thr Leu Ala Asp
1               5

<210> SEQ ID NO 27
<211> LENGTH: 9
<212> TYPE: PRT
<213> ORGANISM: Mus musculus

<400> SEQUENCE: 27

Gln His His Tyr Arg Thr Pro Pro Thr
1               5

<210> SEQ ID NO 28
<211> LENGTH: 5
<212> TYPE: PRT
<213> ORGANISM: Mus musculus

<400> SEQUENCE: 28

Asn Tyr Leu Ile Glu
1               5

<210> SEQ ID NO 29
<211> LENGTH: 17
<212> TYPE: PRT
<213> ORGANISM: Mus musculus

<400> SEQUENCE: 29

Met Ile Asn Pro Gly Ser Gly Asp Thr Asn Phe Asn Glu Lys Phe Lys
1               5                   10                  15

Ala

<210> SEQ ID NO 30
<211> LENGTH: 8
<212> TYPE: PRT
<213> ORGANISM: Mus musculus

<400> SEQUENCE: 30

Ser Ser Gln Leu Gly Leu Pro Tyr
1               5

<210> SEQ ID NO 31
<211> LENGTH: 106
<212> TYPE: PRT
<213> ORGANISM: Mus musculus

<400> SEQUENCE: 31

Asp Ile Gln Met Thr Gln Ser Pro Ser Leu Ser Ala Ser Leu Gly
1               5                   10                  15

Asp Lys Val Thr Ile Thr Cys Lys Ala Ser Gln Asp Ile Asn Lys Tyr
                20                  25                  30

Ile Asp Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Val Gln Tyr Asp Asp Leu Trp Thr
                85                  90                  95

Phe Gly Gly Gly Thr Lys Leu Glu Ile Lys
            100                 105

<210> SEQ ID NO 32
<211> LENGTH: 111
<212> TYPE: PRT
<213> ORGANISM: Mus musculus

<400> SEQUENCE: 32

Gln Val Gln Leu Lys Gln Ser Gly Pro Ser Leu Val Gln Pro Ser Gln
1               5                   10                  15

Ser Leu Ser Ile Thr Cys Thr Val Ser Gly Phe Ser Leu Thr Ser Tyr
                20                  25                  30

Gly Val His Trp Val Arg Gln Ser Pro Gly Lys Gly Leu Glu Trp Leu
            35                  40                  45

Gly Val Ile Trp Arg Gly Gly Ser Thr Asp Tyr Asn Ala Ala Phe Met
        50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Asn His Arg Asp Trp Gly Gln Gly Thr Leu Val Thr Val Ser Ala
            100                 105                 110

<210> SEQ ID NO 33
<211> LENGTH: 106
<212> TYPE: PRT
<213> ORGANISM: Mus musculus

<400> SEQUENCE: 33

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Asp Trp Tyr Gln His Lys Pro Gly Lys Ser Pro Arg Leu Leu Ile
        35                  40                  45

His Tyr Ala Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asp Leu Trp Thr
                85                  90                  95

Phe Gly Gly Gly Thr Lys Leu Glu Ile Lys
            100                 105

<210> SEQ ID NO 34
<211> LENGTH: 111
<212> TYPE: PRT
<213> ORGANISM: Mus musculus

<400> SEQUENCE: 34

Gln Val Gln Leu Lys Gln Ser Gly Pro Ser Leu Leu Gln Pro Ser Gln
1               5                   10                  15

Ser Leu Ser Ile Thr Cys Thr Val Ser Gly Phe Ser Leu Thr Ser Tyr
            20                  25                  30

Gly Ile His Trp Val Arg Gln Ser Pro Gly Lys Gly Leu Glu Trp Leu
        35                  40                  45

Gly Val Ile Trp Arg Gly Gly Ile Thr Asp Tyr Asn Ala Pro Phe Met
    50                  55                  60

Ser Arg Leu Asn Ile Thr Lys Asp Asn Ser Lys Asn Gln Val Phe Phe
65                  70                  75                  80

Lys Met Asn Ser Leu Gln Val Asp Asp Thr Ala Ile Tyr Tyr Cys Ala
                85                  90                  95

Asn His Arg Asp Trp Gly Gln Gly Thr Leu Val Thr Val Ser Ala
            100                 105                 110

<210> SEQ ID NO 35
<211> LENGTH: 111
<212> TYPE: PRT
<213> ORGANISM: Mus musculus

<400> SEQUENCE: 35

Asp Ile Val Leu Thr Gln Ser Pro Ala Ser Leu Val Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Thr Thr Ser Asn Gln Gly Ser Gly Val Arg Ala
    50                  55                  60

Arg Leu Ser Gly Ser Gly Cys Gly Thr Asp Phe Ser Leu Asn Ile His
65                  70                  75                  80

```
Pro Met Glu Glu Asp Asp Ser Ala Met Tyr Phe Cys Gln Gln Ser Lys
                85                  90                  95

Glu Val Pro Tyr Thr Phe Gly Gly Gly Thr Lys Leu Glu Ile Lys
            100                 105                 110

<210> SEQ ID NO 36
<211> LENGTH: 120
<212> TYPE: PRT
<213> ORGANISM: Mus musculus

<400> SEQUENCE: 36

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Val Glu Trp
            35                  40                  45

Met Gly Tyr Ile Ser Tyr Ser Gly Ser Ser Tyr Asn Pro Ser Leu
        50                  55                  60

Lys Gly Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Phe Tyr Tyr Arg Phe Asp Ala Tyr Phe Asp Ser Trp Gly Gln
            100                 105                 110

Gly Thr Thr Leu Thr Val Ser Ser
        115                 120

<210> SEQ ID NO 37
<211> LENGTH: 111
<212> TYPE: PRT
<213> ORGANISM: Mus musculus

<400> SEQUENCE: 37

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
                20                  25                  30

Gly Thr Ser Leu Met His Trp Tyr Gln His Lys Pro Gly Gln Thr Pro
            35                  40                  45

Lys Leu Leu Ile Tyr Ser Gly Ser Asn Val Glu Ser Gly Val Pro Ala
        50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Glu Val Pro Ser Thr Phe Gly Gly Gly Thr Lys Leu Glu Ile Lys
            100                 105                 110

<210> SEQ ID NO 38
<211> LENGTH: 119
<212> TYPE: PRT
<213> ORGANISM: Mus musculus
```

<400> SEQUENCE: 38

Asp Val Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Thr Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu His Leu Asn Ser Val Ile Thr Glu Asp Thr Ala Thr Tyr Tyr Cys
                85                  90                  95

Ala Arg Arg Glu Gly His Tyr Ser Trp Phe Pro Tyr Trp Gly Gln Gly
            100                 105                 110

Thr Leu Val Thr Val Ser Ala
        115

<210> SEQ ID NO 39
<211> LENGTH: 107
<212> TYPE: PRT
<213> ORGANISM: Mus musculus

<400> SEQUENCE: 39

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Glu Asn Ser Pro Gln Leu Leu Val
        35                  40                  45

Tyr Asn Ala Tyr Thr Leu Ala Asp Gly Val Pro Ser Arg Phe Ser Gly
    50                  55                  60

Ser Gly Ser Gly Thr Gln Phe Ser Leu Lys Ile Ile Ser Leu Gln Pro
65                  70                  75                  80

Glu Asp Phe Gly Asn Tyr Tyr Cys Gln His His Tyr Arg Thr Pro Pro
                85                  90                  95

Thr Phe Gly Gly Gly Thr Lys Leu Glu Ile Lys
            100                 105

<210> SEQ ID NO 40
<211> LENGTH: 117
<212> TYPE: PRT
<213> ORGANISM: Mus musculus

<400> SEQUENCE: 40

Gln Val Gln Leu Gln Gln Ser Gly Ala Val Leu Val Arg Pro Gly Thr
1               5                   10                  15

Ser Ile Lys Val Ser Cys Lys Ala Ser Gly Tyr Ala Phe Thr Asn Tyr
            20                  25                  30

Leu Ile Glu Trp Ile Lys Lys Arg Pro Gly Gln Gly Leu Glu Trp Ile
        35                  40                  45

Gly Met Ile Asn Pro Gly Ser Gly Asp Thr Asn Phe Asn Glu Lys Phe
    50                  55                  60

Lys Ala Lys Ala Thr Leu Thr Ala Asp Lys Ser Ser Thr Thr Ala Tyr
65                  70                  75                  80

```
Met Gln Leu Asn Ser Leu Thr Phe Asp Asp Ser Ala Val Tyr Phe Cys
             85                  90                  95

Ala Arg Ser Ser Gln Leu Gly Leu Pro Tyr Trp Gly Gln Gly Thr Leu
            100                 105                 110

Val Thr Val Ser Ala
        115

<210> SEQ ID NO 41
<211> LENGTH: 2079
<212> TYPE: DNA
<213> ORGANISM: Homo sapiens

<400> SEQUENCE: 41
atgggcaccg tcagctccag gcggtcctgg tggccgctgc cactgctgct gctgctgctg      60
ctgctcctgg gtcccgcggg cgccgtgcg caggaggacg aggacggcga ctacgaggag      120
ctggtgctag ccttgcgttc cgaggaggac ggcctggccg aagcacccga gcacggaacc      180
acagccacct ccaccgctg cgccaaggat ccgtggaggt tgcctggcac ctacgtggtg      240
gtgctgaagg aggagaccca cctctcgcag tcagagcgca ctgcccgccg cctgcaggcc      300
caggctgccc gccggggata cctcaccaag atcctgcatg tcttccatgg ccttcttcct      360
ggcttcctgg tgaagatgag tggcgacctg ctggagctgg ccttgaagtt gccccatgtc      420
gactacatcg aggaggactc ctctgtcttt gcccagagca tcccgtggaa cctggagcgg      480
attccccctc cacggtaccg gcggatgaa taccagcccc ccgacggagg cagcctggtg      540
gaggtgtatc tcctagacac cagcatacag agtgaccacc gggaaatcga gggcagggtc      600
atggtcaccg acttcgagaa tgtgcccgag gaggacggga cccgcttcca cagacaggcc      660
agcaagtgtg acagtcatgg cacccacctg caggggtgg tcagcggccg ggatgccggc      720
gtggccaagg gtgccagcat gcgcagcctg cgcgtgctca actgccaagg aaggggcacg      780
gttagcggca ccctcatagg cctggagttt attcggaaaa gccagctggt ccagcctgtg      840
gggccactgg tggtgctgct gccctggcg ggtgggtaca ccgcgtcct caacgccgcc      900 tgccagcgcc tggcgagggc tggggtcgtg ctggtcaccg ctgccggcaa cttccgggac      960
gatgcctgcc tctactcccc agcctcagct cccgaggtca tcacagttgg ggccaccaat     1020
gcccaggacc agccggtgac cctggggact tggggaccaa actttggccg ctgtgtggac     1080
ctctttgccc caggggagga catcattggt gcctccagcg actgcagcac ctgctttgtg     1140
tcacagagtg ggacatcaca ggctgctgcc cacgtggctg gcattgcagc catgatgctg     1200
tctgccgagc cggagctcac cctggccgag ttgaggcaga gactgatcca cttctctgcc     1260
aaagatgtca tcaatgaggc ctggttccct gaggaccagc gggtactgac ccccaacctg     1320
gtggccgccc tgcccccag cacccatggg gcaggttggc agctgttttg caggactgtg     1380
tggtcagcac actcggggcc tacacggatg ccacagcca tcgcccgctg cgccccagat     1440
gaggagctgc tgagctgctc cagtttctcc aggagtggga gcggcgggg cgagcgcatg     1500 gaggcccaag ggggcaagct ggtctgccgg gcccacaacg cttttgggg tgagggtgtc     1560 tacgccattg ccaggtgctg cctgctaccc caggccaact gcagcgtcca cacagctcca     1620
ccagctgagg ccagcatggg gacccgtgtc cactgccacc aacagggcca cgtcctcaca     1680
ggctgcagct cccactggga ggtggaggac cttggcaccc acaagccgcc tgtgctgagg     1740
ccacgaggtc agcccaacca gtgcgtgggc cacagggagg ccagcatcca cgcttcctgc     1800
tgccatgccc caggtctgga atgcaaagtc aaggagcatg gaatcccggc ccctcaggag     1860
```

-continued

```
caggtgaccg tggcctgcga ggagggctgg accctgactg gctgcagtgc cctccctggg      1920
acctcccacg tcctggggc ctacgccgta gacaacacgt gtgtagtcag gagccgggac       1980
gtcagcacta caggcagcac cagcgaagag gccgtgacag ccgttgccat ctgctgccgg      2040
agccggcacc tggcgcaggc ctcccaggag ctccagtga                             2079
```

<210> SEQ ID NO 42
<211> LENGTH: 2365
<212> TYPE: DNA
<213> ORGANISM: Homo sapiens

<400> SEQUENCE: 42

```
atggggccct ggggctggaa attgcgctgg accgtcgcct tgctcctcgc cgcggcgggg      60
actgcagtgg cgacagatg cgaaagaaac gagttccagt gccaagacgg gaaatgcatc     120
tcctacaagt gggtctgcga tggcagcgct gagtgccagg atggctctga tgagtcccag     180
gagacgtgct tgtctgtcac ctgcaaatcc ggggacttca gctgtggggg ccgtgtcaac     240
cgctgcattc ctcagttctg gaggtgcgat ggccaagtgg actgcgacaa cggctcagac     300
gagcaaggct gtcccccaa gacgtgctcc caggacgagt ttcgctgcca cgatgggaag     360
tgcatctctc ggcagttcgt ctgtgactca gaccgggact gcttggacgg ctcagacgag     420
gcctcctgcc cggtgctcac ctgtggtccc gccagcttcc agtgcaacag ctccacctgc     480 atccccagc tgtgggcctg cgacaacgac ccgactgcg aagatggctc ggatgagtgg      540
ccgcagcgct gtaggggtct ttacgtgttc caaggggaca gtagcccctg ctcggccttc     600
gagttccact gcctaagtgg cgagtgcatc cactccagct ggcgctgtga tggtggcccc     660
gactgcaagg acaaatctga cgaggaaaac tgcgctgtgg ccacctgtcg ccctgacgaa     720
ttccagtgct ctgatggaaa ctgcatccat ggcagccggc agtgtgaccg ggaatatgac     780
tgcaaggaca tgagcgatga agttggctgc gttaatgtga cactctgcga gggacccaac     840
aagttcaagt gtcacagcgg cgaatgcatc accctggaca aagtctgcaa catggctaga     900
gactgccggg actggtcaga tgaacccatc aaagagtgcg ggaccaacga atgcttggac     960
aacaacggcg gctgttccca cgtctgcaat gaccttaaga tcggctacga gtgcctgtgc    1020
cccgacggct tccagctggt ggcccagcga agatgcgaag atatcgatga gtgtcaggat    1080
cccgacacct gcagccagct ctgcgtgaac ctggagggtg gctacaagtg ccagtgtgag    1140
gaaggcttcc agctggaccc ccacacgaag gcctgcaagg ctgtgggctc catcgcctac    1200
ctcttcttca ccaaccggca cgaggtcagg aagatgacgc tggaccggag cgagtacacc    1260
agcctcatcc ccaacctgag gaacgtggtc gctctggaca cggaggtggc cagcaataga    1320
atctactggt ctgaccctgtc ccagagaatg atctgcagca cccagcttga cagagcccac    1380
ggcgtctctt cctatgacac cgtcatcagc agggacatcc aggcccccga cgggctggct    1440
gtggactgga tccacagcaa catctactgg accgactctg tcctgggcac tgtctctgtt    1500
gcggatacca agggcgtgaa gaggaaaacg ttattcaggg agaacggctc caagccaagg    1560
gccatcgtgg tggatcctgt tcatggcttc atgtactgga ctgactgggg aactcctgcc    1620
aagatcaaga aaggggcct gaatggtgtg acatctact cgctggtgac tgaaaacatt     1680
cagtggccca atggcatcac cctagatctc ctcagtggcc gcctctactg ggttgactcc    1740
aaacttcact ccatctcaag catcgatgtc aacgggggca accggaagac catcttggag    1800
gatgaaaaga ggctggccca ccccttctcc ttggccgtct ttgaggacaa agtattttgg    1860
acagatatca tcaacgaagc catttttcagt gccaaccgcc tcacaggttc cgatgtcaac    1920
```

```
ttgttggctg aaaacctact gtccccagag gatatggttc tcttccacaa cctcacccag  1980
ccaagaggag tgaactggtg tgagaggacc accctgagca atggcggctg ccagtatctg  2040
tgcctccctg ccccgcagat caaccccccac tcgcccaagt ttacctgcgc ctgcccggac  2100
ggcatgctgc tggccaggga catgaggagc tgcctcacag aggctgaggc tgcagtggcc  2160
acccaggaga catccaccgt caggctaaag gtcagctcca cagccgtaag gacacagcac  2220
acaaccaccc gacctgttcc cgacacctcc cggctgcctg gggccacccc tgggctcacc  2280
acggtggaga tagtgacaat gtctcaccaa gctctgggcg acgttgctgg cagaggaaat  2340
gagaagaagc ccagtagcgt gaggg                                        2365
```

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 43

```
gtacgctagc caccatgggg ccctgggggct g                                31
```

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 44

```
gatcctcgag ccctcacgct actgg                                        25
```

<210> SEQ ID NO 45
<211> LENGTH: 106
<212> TYPE: PRT
<213> ORGANISM: Artificial Sequence
<220> FEATURE:
<223> OTHER INFORMATION: Description of Artificial Sequence: Synthetic Amino acid sequence of light chain

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Ile Asp Trp Tyr Gln His Lys Pro Gly Lys Ala Pro Lys Leu Leu Ile
        35                  40                  45

His Tyr Ala Ser Thr Leu Gln Pro Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Asp Leu Trp Thr
                85                  90                  95

Phe Gly Gln Gly Thr Lys Val Glu Ile Lys
            100                 105

<210> SEQ ID NO 46
<211> LENGTH: 318
<212> TYPE: DNA
<213> ORGANISM: Artificial Sequence
<220> FEATURE:
<223> OTHER INFORMATION: Description of Artificial Sequence: Synthetic
    Nucleic acid encoding amino acid sequence of light chain

<400> SEQUENCE: 46

```
gacatccaga tgacccagag ccccagcagc ctgagcgcca gcgtgggcga cagagtgacc    60
atcacctgcc aggccagcca ggacatcaac aagtacatcg actggtacca gcacaagccc   120
ggcaaggccc ccaagctgct gatccactac gccagcaccc tgcagcccgg cgtgcccagc   180
agattcagcg gcagcggcag cggcagagac tacaccttca ccatcagcag cctgcagccc   240
gaggacatcg ccacctacta ctgcctgcag tacgacgacc tgtggacctt cggccagggc   300
accaaggtgg agatcaag                                                 318
```

<210> SEQ ID NO 47
<211> LENGTH: 111
<212> TYPE: PRT
<213> ORGANISM: Artificial Sequence
<220> FEATURE:
<223> OTHER INFORMATION: Description of Artificial Sequence: Synthetic
    Amino acid sequence of heavy chain

<400> SEQUENCE: 47

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Phe Ser Ile Ser Ser Tyr
            20                  25                  30

Gly Ile His Trp Ile Arg Gln Ser Pro Gly Lys Gly Leu Glu Trp Ile
        35                  40                  45

Gly Val Ile Trp Arg Gly Gly Ile Thr Asp Tyr Asn Ala Pro Phe Met
    50                  55                  60

Ser Arg Val Thr Ile Ser Lys Asp Asn Ser Lys Asn Gln Val Ser Phe
65                  70                  75                  80

Lys Leu Ser Ser Val Thr Ala Ala Asp Thr Ala Val Tyr Tyr Cys Ala
                85                  90                  95

Asn His Arg Asp Trp Gly Gln Gly Thr Leu Val Thr Val Ser Ser
            100                 105                 110
```

<210> SEQ ID NO 48
<211> LENGTH: 333
<212> TYPE: DNA
<213> ORGANISM: Artificial Sequence
<220> FEATURE:
<223> OTHER INFORMATION: Description of Artificial Sequence: Synthetic
    Nucleic acid encoding amino acid sequence of heavy chain

<400> SEQUENCE: 48

```
caggtgcagc tgcaggaaag cggcccgggc ctggtgaaac cgagccagac cctgagcctg    60
acctgcaccg tgagcggctt tagcattagc agctatggca ttcattggat tcgccagagc   120
ccgggcaaag cctggaatg gattggcgtg atttggcgcg gcggcattac cgattataac   180
gcgccgttta tgagccgcgt gaccattagc aaagataaca gcaaaaacca ggtgagcttt   240
aaactgagca gcgtgaccgc ggcggatacc gcggtgtatt attgcgcgaa ccatcgcgat   300
tggggccagg gcaccctggt gaccgtgagc agc                                333
```

<210> SEQ ID NO 49
<211> LENGTH: 111
<212> TYPE: PRT
<213> ORGANISM: Artificial Sequence
<220> FEATURE:
<223> OTHER INFORMATION: Description of Artificial Sequence: Synthetic
      Amino acid sequence of heavy chain

<400> SEQUENCE: 49

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Ser Ser Tyr
            20                  25                  30

Gly Val His Trp Ile Arg Gln Ser Pro Gly Lys Gly Leu Glu Trp Ile
        35                  40                  45

Gly Val Ile Trp Arg Gly Gly Ser Thr Asp Tyr Asn Ala Ala Phe Met
    50                  55                  60

Ser Arg Val Thr Ile Ser Lys Asp Asn Ser Lys Asn Gln Val Ser Phe
65                  70                  75                  80

Lys Leu Ser Ser Val Thr Ala Ala Asp Thr Ala Val Tyr Tyr Cys Ala
                85                  90                  95

Asn His Arg Asp Trp Gly Gln Gly Thr Leu Val Thr Val Ser Ser
            100                 105                 110
```

<210> SEQ ID NO 50
<211> LENGTH: 333
<212> TYPE: DNA
<213> ORGANISM: Artificial Sequence
<220> FEATURE:
<223> OTHER INFORMATION: Description of Artificial Sequence: Synthetic
      Nucleic acid encoding amino acid sequence of heavy chain

<400> SEQUENCE: 50

```
caggtgcagc tgcaggaaag cggcccgggc ctggtgaaac cgagccagac cctgagcctg      60
acctgcaccg tgagcggctt tagcattagc agctatggcg tgcattggat tcgccagagc     120
ccgggcaaag gcctggaatg gattggcgtg atttggcgcg gcggcagcac cgattataac     180
gcggcgttta tgagccgcgt gaccattagc aaagataaca gcaaaaacca ggtgagcttt     240
aaactgagca gcgtgaccgc ggcggatacc gcggtgtatt attgcgcgaa ccatcgcgat     300
tggggccagg gcaccctggt gaccgtgagc agc                                  333
```

<210> SEQ ID NO 51
<211> LENGTH: 6
<212> TYPE: PRT
<213> ORGANISM: Mus musculus

<400> SEQUENCE: 51

```
His Arg Asp Asp Asp Asp
1               5
```

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

```
gtacactagt caccatgggc accgtcagct c                                     31
```

<210> SEQ ID NO 53
<211> LENGTH: 28
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 53
gatcctcgag cctggagctc ctgggagg                                         28
```

ANTI-PCSK9 ANTIBODY AND USE THEREOF

CROSS-REFERENCE TO RELATED APPLICATIONS

This application is a 35 U.S.C. 371 national stage of PCT/CN2016/107042 filed on Nov. 24, 2016, which claims priority to Chinese application No. 201510846855, filed on Nov. 27, 2015, the contents of which are fully incorporated herein by reference.

REFERENCE TO SUBMISSION OF A SEQUENCE LISTING AS A TEXT FILE

The Sequence Listing written in file 088448-1088269-005000US_SL.txt created on Sep. 4, 2018, 27,238 bytes, machine format IBM-PC, MS-Windows operating system, is hereby incorporated by reference in its entirety for all purposes.

TECHNICAL FIELD

The present invention belongs to the field of biomedicine. Provided herein is an antigenic polypeptide, which can be used for producing antibodies capable of binding to PCSK9-derived molecules. The invention also relates to an antibody or a functional fragment thereof specifically binding to PCSK9 with high affinity. The invention also provides a nucleic acid molecule encoding the present antibody or the functional fragment thereof, an expression vector and a host cell for expressing the present antibody or the functional fragment thereof, and the production method of the present antibody or the functional fragment thereof. The invention also provides an immunoconjugate and a pharmaceutical composition comprising the present antibody or the functional fragment thereof, and a method for treating various diseases including dyslipidemia and related cardiovascular diseases by using the present antibody or the functional fragment thereof.

BACKGROUND TECHNOLOGY

Familial hypercholesteremia (FH) is an autosomal monogenic dominant genetic disease, which is familial and has various clinical performances. FH is the most serious one among lipid metabolism monogenic diseases, and is also referred to as LDL receptor disease or hyperlipidaemia type IIa, which is the most common inherited hyperlipidaemia in children, and is an important risk factor of coronary artery disease. The significant increase of Low-density lipoprotein cholesterol (LDL-C) is an important sign of the disease, and therefore, inhibiting the degradation of the hepatocytic LDLR and increasing the LDL uptake of LDLR can reduce the atherosclerosis progress, and the risk of disease can be reduced. PCSK9 gene mutations (S127R,F216L) were detected in ADH patient's family from which LDLR and apoB gene mutations were excluded. The effect of PCSK9 on lipid metabolism was illustrated for the first time (Abifadel, Varret et al. 2003). At present, PCSK9 is taken as a novel therapeutic target for dyslipidemia, and has a good application prospect.

Proprotein convertase subtilisin/kexin 9(PCK9), also referred to as neural apoptosis-regulated convertase 1 (NARC-1), belongs to the ninth member of the Kexin-like proprotein convertase subtilisin family, and is composed of 692 amino acid residues, mainly found in liver, kidney, and small intestine and the like. It is expressed by liver parenchyma cells, mesenchymal cells, and colon epidermal cells and the like, and is found in blood as a secretory protein (Seidah, Benjannet et al. 2003).

Pcsk9 is encoded by PCSK9 gene, which is located on human autosomal LP33-p34.3, and is mainly synthesized in endoplasmic reticulum. It first forms a 72 kDa non-active precursor structure, and then cleavage occurs at positions 152 and 153 via autocatalysis, to form a 14 kDa precursor domain and a 57 kDa mature fragment comprising a catalytic domain and a C-terminal domain (Benjannet, Rhaids et al. 2004). The precursor domain can bind to the catalytic domain in a non-covalent fashion, which is necessary for correctly folding of mature fragment and transporting out of the endoplasmic reticulum.

PCSK9 gene mutation can be divided into a function acquired type (D347Y, S127R, F216L, L82X, and Y142X, etc.) and a function defected type (R46L, Y142X, and C679) (Abifadel, Varret et al. 2003), wherein through the synergy with different proteins, the function acquired type mutants can change the affinity of the PCSK9, or improve the sensitivity of protease to the self-cleavage of PCSK9, and improve the degradation of LDLR by PCSK9, resulting in increased blood LDL-C level, inducing ADH or early-onset atherosclerosis disease.

Research shows that PCSK9 not only has an important influence on differentiation of liver parenchyma cells and nerve cells (Seidah, Benjannet et al. 2003), but also adjusts the expression of low-density lipoprotein receptor (LDLR), so as to participate in synthesis and metabolism of cholesterol. Research shows that adding purified PCSK9 protein into HepG2 cell culture medium reduced cell surface LDLR with a dose dependent effect (Lagace, Curtis et al. 2006). However, the level of LDLR was significantly reduced in mice with liver cells over-expressing PCSK9, while the expression level of LDLR mRNA was not reduced (Lambert, Charlton et al. 2009). Therefore, PCSK9 adjusts LDLR level by a post-transcription mechanism.

LDLR molecule consisted of five main domains: a ligand-binding cysteine-rich region; an epidermal growth factor (EGF) precursor homologous domain, including three EGF-like repeat sequences (EGF-A, EGF-B, and EGF-C) and a beta helix structure, a saccharide domain, a transmembrane domain, and a cytoplasmic tail region containing a sequence necessary for receptor internalization.

In 2007, a breakthrough progress was made with respect to the study of molecular mechanism of PCSK9-mediated LDLR degradation. The study shows that PCSK9 is secreted into blood plasma, which can bind to the extracellular domain of LDLR and cause internalization, facilitating the degradation of the latter in lysosome (Zhang, Lagace et al. 2007). Further research showed that in neutral pH environment at cell surface, PCSK9 can bind to EGF-A on the extracellular segment of LDLR, causing endocytosis into the cell. In low-pH cellular environment, the C-terminal domain of PCSK9 can bind to the ligand domain of LDLR, so that LDLR is degraded in lysosome and unable to return to cell membrane (Fisher, Surdo et al. 2007).

In conclusion, PCSK9 has become an important target of dyslipidemia and the related cardiovascular diseases at present. The monoclonal antibody against such has a wide application prospect.

SUMMARY OF INVENTION

The Problem to be Solved by the Invention

One object of the present invention is to provide an antibody against a dyslipidemia-related target and a functional fragment thereof, a method for treating dyslipidemia by using the antibody or the antibody functional fragment thereof, and the like.

Means for Solving the Technical Problem

In order to achieve the above mentioned objects, the inventors of the invention performed thorough research, and completed the present invention based on the findings that the present antibody can specifically bind to PCSK9 and inhibit the binding of PCSK9 to LDLR, so as to increase the uptake of LDL-c. The present invention comprises the following aspects.

In one aspect, the invention provides anti-PCSK9 antibodies capable of binding to proprotein convertase subtilisin/kexin 9(PCK9), and functional fragments thereof, comprising the heavy chain CDRs of an amino acid sequence selected from the group consisting of SEQ ID NOs: 4, 5, 6, 10, 11, 12, 16, 17, 18, 22, 23, 24, 28, 29, and 30 or any of the variants of the sequence, and/or the light chain CDRs of an amino acid sequence selected from the group consisting of SEQ ID NOs: 1, 2, 3, 7, 8, 9, 13, 14, 15, 19, 20, 21, 25, 26, and 27 or any of the variants of the sequence.

In another aspect, the invention further provides antibodies capable of binding to PCSK9 or functional fragments thereof, wherein the amino acid sequences of CDR1, CDR2, and CDR3 of the heavy chain CDRs are selected from one of the groups consisting of the following amino acid sequences or variants thereof:

|   | HCDR1 | HCDR2 | HCDR3 |
|---|---|---|---|
| A | SEQ ID NO: 4 | SEQ ID NO: 5 | SEQ ID NO: 6 |
| B | SEQ ID NO: 10 | SEQ ID NO: 11 | SEQ ID NO: 12 |
| C | SEQ ID NO: 16 | SEQ ID NO: 17 | SEQ ID NO: 18 |
| D | SEQ ID NO: 22 | SEQ ID NO: 23 | SEQ ID NO: 24 |
| E | SEQ ID NO: 28 | SEQ ID NO: 29 | SEQ ID NO: 30 | and/or the amino acid sequences of CDR1, CDR2, and CDR3 of the light chain CDRs are selected from the group consisting of the following amino acid sequences or variants thereof.

|   | LCDR1 | LCDR2 | LCDR3 |
|---|---|---|---|
| A | SEQ ID NO: 1 | SEQ ID NO: 2 | SEQ ID NO: 3 |
| B | SEQ ID NO: 7 | SEQ ID NO: 8 | SEQ ID NO: 9 |
| C | SEQ ID NO: 13 | SEQ ID NO: 14 | SEQ ID NO: 15 |
| D | SEQ ID NO: 19 | SEQ ID NO: 20 | SEQ ID NO: 21 |
| E | SEQ ID NO: 25 | SEQ ID NO: 26 | SEQ ID NO: 27 |

In another aspect, the present invention provides antibody capable of binding to PCSK9 and the functional fragment thereof, wherein the amino acid sequences of the heavy chain CDR1, CDR2 and CDR3 and the light chain CDR1, CDR2 and CDR3 are selected from the group consisting of the following amino acid sequences or variants thereof:

|   | LCDR1 | LCDR2 | LCDR3 | HCDR1 | HCDR2 | HCDR3 |
|---|---|---|---|---|---|---|
| A | SEQ ID NO: 1 | SEQ ID NO: 2 | SEQ ID NO: 3 | SEQ ID NO: 4 | SEQ ID NO: 5 | SEQ ID NO: 6 |
| B | SEQ ID NO: 7 | SEQ ID NO: 8 | SEQ ID NO: 9 | SEQ ID NO: 10 | SEQ ID NO: 11 | SEQ ID NO: 12 |
| C | SEQ ID NO: 13 | SEQ ID NO: 14 | SEQ ID NO: 15 | SEQ ID NO: 16 | SEQ ID NO: 17 | SEQ ID NO: 18 |
| D | SEQ ID NO: 19 | SEQ ID NO: 20 | SEQ ID NO: 21 | SEQ ID NO: 22 | SEQ ID NO: 23 | SEQ ID NO: 24 |
| E | SEQ ID NO: 25 | SEQ ID NO: 26 | SEQ ID NO: 27 | SEQ ID NO: 28 | SEQ ID NO: 29 | SEQ ID NO: 30 |

In another aspect, the invention provides antibodies capable of binding to PCSK9 or functional fragments thereof, which comprises a heavy chain variable region selected from the group consisting of the amino acid sequences of SEQ ID NOs: 32, 34, 36, 38, and 40 or variants of any of said sequences, and/or a light chain variable region selected from the group consisting of the amino acid sequences of SEQ ID NOs: 31, 33, 35, 37, and 39 or variants of said sequences.

In another aspect, the invention provides antibodies capable of binding to PCSK9 or functional fragments thereof, wherein said heavy chain variable region is SEQ ID NO: 32 or a variant thereof and said light chain variable region is SEQ ID NO: 31 or a variant thereof, or the heavy chain variable region is SEQ ID NO: 34 or a variant thereof and the light chain variable region is SEQ ID NO: 33 or a variant thereof, or the heavy chain variable region is SEQ ID NO:36 or a variant thereof and the light chain variable region is SEQ ID NO:35 or a variant thereof, or the heavy chain variable region is SEQ ID NO:38 or a variant thereof and the light chain variable region is SEQ ID NO: 37 or a variant thereof, or the heavy chain variable region is SEQ ID NO: 40 or a variant thereof and the light chain variable region is SEQ ID NO: 39 or a variant thereof.

In another aspect, the invention provides antibodies capable of binding to PCSK9 or functional fragments thereof, which is a chimeric antibody, a humanized antibody, or a fully human antibody.

In another aspect, the invention provides an isolated nucleic acid molecule encoding the antibody capable of binding to PCSK9 or a functional fragment thereof and an expression vector or a host cell comprising the nucleic acid molecule.

In another aspect, the invention provides a pharmaceutical composition, comprising the antibody capable of binding to PCSK9 or the functional fragment thereof, a nucleic acid molecule encoding the present antibody capable of binding to PCSK9 or the functional fragment thereof, and an expression vector or a host cell, or any combination thereof, and a pharmaceutically acceptable carrier.

In another aspect, the present invention provides use of the present antibody capable of binding to PCSK9 or a functional fragment thereof, or the nucleic acid molecule encoding the same, or an expression vector or a host cell in the manufacture of a medicament for treating diseases such as dyslipidemia and related cardiovascular diseases, including hyperlipidemia or hypercholesterolemia.

In another aspect, the present invention provides the use of the present antibody capable of binding to PCSK9 or a functional fragment thereof, or the nucleic acid molecule encoding the same, or an expression vector or a host cell in the manufacture of a medicament for facilitating cellular uptake of LDL. (According to the description of the background art, it is understood that PCSK9 can bind to LDLR and reduce LDLR, so that the cell uptake of LDL is reduced, causing rise of blood lipids. An anti-PCSK9 antibody can neutralize PCSK9 thereby reversing the process, improving cell uptake of LDL and reduce blood lipids.)

In another aspect, the present invention provides an immunoconjugate, which comprises the present antibody capable of binding to PCSK9 or a functional fragment thereof conjugated to a therapeutic agent, preferably, the therapeutic agent is a toxin, a radioactive isotope, a drug or a cytotoxic agent.

SPECIFIC MODE FOR CARRYING OUT THE INVENTION

Figure 1:
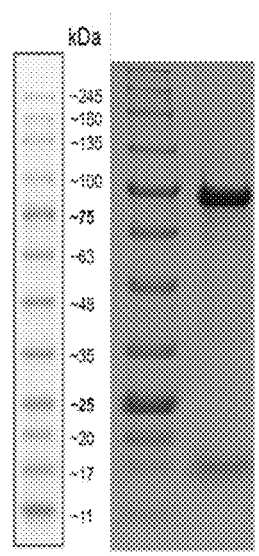
FIG. 1: SDS-PAGE electrophoresis diagram of human PCSK9.

Unless otherwise defined, all scientific and technological terms used herein have the same meaning as understood by one of ordinary skill in the art. For the definition and the terminology in relevant art, the skilled in the art can refer to Current Protocols In Molecular Biology (Ausubel). The abbreviations of the amino acid residues are standard 3-letter and/or 1-letter code accepted in the field, referring to one of the 20 common L-amino acids.

The invention provides an anti-PCSK9 antibody or the functional fragment thereof capable of binding to proprotein convertase subtilisin/kexin 9(PCK9). The present antibody or the functional fragment thereof has at least one of the capabilities including blocking the interaction between PCSK9 and LDLR with high affinity; binding to PCSK9 with high specificity.

The invention further provides a humanized anti-PCSK9 antibody and a functional fragment thereof. The humanized antibody is obtained by carrying out computer simulation design on a murine-derived antibody generated by immunizing mice, combined with phage display technology. The binding epitopes are also correspondingly identified according to the binding characteristics with PCSK9 proteins from different species. The present humanized anti-PCSK9 antibody and the functional fragment thereof not only has the above-mentioned beneficial characteristics, but also binds to human or Cynomolgus monkey PCSK9 protein with high affinity and interacts with murine-derived PCSK9 protein.

The skilled in the art can replace, add and/or delete one or more (e.g., 1, 2, 3, 4, 5, 6, 7, 8, 9 or 10 or more) amino acids of the sequences described in the present invention provided that the antibody activity is not substantially affected so as to obtain a variant of the sequence of the antibody or the functional fragment thereof, which are considered to be included within the scope of the present invention. For example, amino acids in the variable region can be replaced with those having similar properties. The variants of the present invention can have a sequence having at least 95%, 96%, 97%, 98% or 99% sequence identity with the sequence from which the variant is derived. The sequence identity can be measured by using sequence analysis software, for example, computer program BLAST with default parameters, especially BLASTP or TBLASTN.

The antibody of the invention can be of full-length (e.g., IgG1 or IgG4 antibody) or can only comprise an antigen binding moiety (e.g., Fab, F (ab')2 or scFv fragment) or can be modified to alter the function. The invention comprises an anti-PCSK9 antibody with a modified glycosylation pattern. In some applications, modification for removal of undesirable glycosylation sites may be useful, or the absence of fucose moiety on the oligosaccharide chain, so as to enhance the antibody-dependent cytotoxicity (ADCC). In other applications, it can be modified with galactosyl moiety to modify the complement-dependent cell toxicity (CDC).

The term "functional fragment" as used herein refers to an antibody fragment, such as fv, scFv (sc means single chain), Fab, F(ab')$_2$, Fab', scFv-Fc fragment or diabody), or any fragment which can increase the half-life period by chemical modification or incorporating into liposome. The chemical modification is, for example, addition of poly (alkylene) glycol such as polyethylene glycol ("PEGylated"), (the PEGylated fragments which are referred to as fv-PEG, scFv-PEG, FAB-PEG, F(ab')2-PEG or Fab'-PEG) (wherein "PEG" is polyethylene glycol), and the fragment has an EGFR binding activity. Preferably, the functional fragments consist of or comprise partial sequence of the heavy or light variable chains of their source antibody, wherein the partial sequence is sufficient to retain the same binding specificity and sufficient affinity as the source antibody thereof, for PCSK9, an affinity preferably equal to at least 1/100 of the affinity of the source antibody thereof, in a more preferred manner, equal to at least 1/10. Such functional segments will comprise at least five amino acids, preferably 10, 15, 25, 50 and 100 consecutive amino acids of the source antibody sequence.

One skilled in the art can clone the DNA molecules encoding the anti-PCSK9 antibody of the present invention into a vector, and then transform vector into a host cell. Therefore, the invention further provides a recombinant DNA vector comprising the DNA molecule encoding the anti-PCSK9 antibody disclosed by the invention.

Preferably, the recombinant DNA vector is an expression vector. The skilled in the art can clone the DNA molecule of the antibody into an expression vector, and transform the vector into a host cell, to obtain an antibody through an inductive expression. The expression vector of the present invention comprises a DNA sequence encoding the heavy chain variable region, light chain variable region and/or constant region of the anti-PCSK9 antibody. However, two expression vectors can be constructed separately, with one comprising a heavy chain variable region and a constant region, and the other one comprising a light chain variable region and a constant region to co-transfect mammal cells. In a preferred embodiment, the expression vector further comprises a promoter and a DNA sequence encoding a secretory signal peptide, and at least one drug resistant gene for screening.

The present host cell can be a prokaryotic host cell, an eukaryotic host cell or a phage. The prokaryotic host cells can be *Escherichia coli, Bacillus subtilis, Streptomycete* or *Proteus mirabilis* and the like. The eukaryotic host cell can be fungus such as *Pichia pastoris, Saccharomyces cerevisiae* and *schizochytrium*, insect cells such as grassland armyworms and the like, plant cells such as tobacco, mammal cells such as BHK cells, CHO cells, COS cells, myeloma cells and the like. In some embodiments, the host cells of the invention are preferably mammal cells, more preferably BHK cells, CHO cells, NSO cells or COS cells.

The term "pharmaceutical composition" as used herein refers to the combination of at least one drug and optionally pharmaceutically acceptable carriers or accessories that are combined together to achieve some particular purpose. In certain embodiments, the pharmaceutical composition comprises a combination separated in time and/or space, as long as they can act together to achieve the purpose of the invention. For example, components in the pharmaceutical composition (such as antibodies and nucleic acid molecules, nucleic acid molecule combinations and/or conjugates according to the present invention) can be administered as a whole or separately to an object. When the components comprised in the pharmaceutical composition are separately administered to an object, said components can be administered at the same time or sequentially. Preferably, the pharmaceutical carrier is water, buffering aqueous solution, isotonic saline solution such as PBS (phosphate buffer solution), glucose, mannitol, dextrose, lactose, starch, magnesium stearate, cellulose, magnesium carbonate, 0.3% glycerol, hyaluronic acid, ethanol or polyalkylene glycol such as polypropylene glycol, triglycerides and the like. The type of the pharmaceutically acceptable carrier especially depends on whether the composition according to the invention is formulated for oral, nasal, subcutaneous, intramuscular or intravenous administration. The composition of the invention can comprise wetting agent, emulsifier or buffer substance as additives.

The pharmaceutical composition according to the invention can be administered by any suitable means, such as oral, nasal, intradermal, subcutaneous, intramuscular or intravenous administration.

In one related aspect, the invention provides a pharmaceutical composition for combination of an anti-PC SK9 antibody and a second therapeutic agent. In one embodiment, the second therapeutic agent is any reagent that can advantageously combine with anti-PCSK9 antibody. Exemplary reagents that may advantageously combine with anti-PC SK9 antibodies include, but are not limited to, other reagents that inhibit PCSK9 activity (including other antibodies or antigen binding fragments thereof, a peptide inhibitor, a small molecule antagonist and the like) and/or a reagent for interfering the upstream or downstream signaling of PCSK9.

The term used herein "eliminating, inhibiting or reducing the PCSK9 activity to prevent or treat diseases or conditions" means diseases or conditions caused by PCSK9 expression or with symptoms/features by PCSK9 expression. In some embodiments, the disease or condition is selected from hyperlipidemia or hypercholesterolemia.

As used herein, a "therapeutically effective amount" refers to a dose sufficient to display the benefit on the subject to which it is administered. The actual amount, as well as the rate and time of administration, will depend on the own conditions of the patient and severity of the condition. The prescription of treatment (such as determination of dose and the like) is finally responsibility of general practitioner and other doctors and depend on his decision, generally considering the disease to be treated, the condition of the individual patient, delivery location, administration means and other factors known to doctors.

The term "subject" as used herein refers to a mammal, such as a human, but also can be other animals such as wild animals (such as heron, stork, crane and the like), livestock (such as ducks, geese and the like) or experimental animals (such as orangutan, monkey, rat, mouse, rabbit, guinea pig and the like).

On one hand, the present antibody or the functional fragment thereof comprises the heavy chain CDRs of an amino acid sequence selected from the group consisting of SEQ ID NOs: 4, 5, 6, 10, 11, 12, 16, 17, 18, 22, 23, 24, 28, 29, and 30 or any of the variants of the sequence, and/or the light chain CDRs of an amino acid sequence selected from the group consisting of SEQ ID NOs: 1, 2, 3, 7, 8, 9, 13, 14, 15, 19, 20, 21, 25, 26, and 27 or any of the variants of the sequence.

In some preferred embodiments, the amino acid sequences of CDR1, CDR2, and CDR3 of the heavy chain CDRs are selected from one of the groups consisting of the following amino acid sequences or variants thereof:

|   | HCDR1 | HCDR1 | HCDR1 |
|---|---|---|---|
| A | SEQ ID NO: 4 | SEQ ID NO: 5 | SEQ ID NO: 6 |
| B | SEQ ID NO: 10 | SEQ ID NO: 11 | SEQ ID NO: 12 |
| C | SEQ ID NO: 16 | SEQ ID NO: 17 | SEQ ID NO: 18 |
| D | SEQ ID NO: 22 | SEQ ID NO: 23 | SEQ ID NO: 24 |
| E | SEQ ID NO: 28 | SEQ ID NO: 29 | SEQ ID NO: 30 | and/or the amino acid sequences of CDR1, CDR2, and CDR3 of the light chain CDRs are selected from the group consisting of the following amino acid sequences or variants thereof.

|   | LCDR1 | LCDR2 | LCDR3 |
|---|---|---|---|
| A | SEQ ID NO: 1 | SEQ ID NO: 2 | SEQ ID NO: 3 |
| B | SEQ ID NO: 7 | SEQ ID NO: 8 | SEQ ID NO: 9 |
| C | SEQ ID NO: 13 | SEQ ID NO: 14 | SEQ ID NO: 15 |
| D | SEQ ID NO: 19 | SEQ ID NO: 20 | SEQ ID NO: 21 |
| E | SEQ ID NO: 25 | SEQ ID NO: 26 | SEQ ID NO: 27 |

In some preferred embodiments, the amino acid sequences of the heavy chain CDR1, CDR2 and CDR3 and the light chain CDR1, CDR2 and CDR3 are selected from the group consisting of the following amino acid sequences or variants thereof:

|   | LCDR1 | LCDR2 | LCDR3 | HCDR1 | HCDR2 | HCDR3 |
|---|---|---|---|---|---|---|
| A | SEQ ID NO: 1 | SEQ ID NO: 2 | SEQ ID NO: 3 | SEQ ID NO: 4 | SEQ ID NO: 5 | SEQ ID NO: 6 |
| B | SEQ ID NO: 7 | SEQ ID NO: 8 | SEQ ID NO: 9 | SEQ ID NO: 10 | SEQ ID NO: 11 | SEQ ID NO: 12 |
| C | SEQ ID NO: 13 | SEQ ID NO: 14 | SEQ ID NO: 15 | SEQ ID NO: 16 | SEQ ID NO: 17 | SEQ ID NO: 18 |
| D | SEQ ID NO: 19 | SEQ ID NO: 20 | SEQ ID NO: 21 | SEQ ID NO: 22 | SEQ ID NO: 23 | SEQ ID NO: 24 |
| E | SEQ ID NO: 25 | SEQ ID NO: 26 | SEQ ID NO: 27 | SEQ ID NO: 28 | SEQ ID NO: 29 | SEQ ID NO: 30 |

In some embodiments, the antibodies or functional fragments thereof of the present invention comprises a heavy chain variable region selected from the group consisting of the amino acid sequences of SEQ ID NOs: 32, 34, 36, 38, and 40 or variants of any of said sequences, and/or light chain variable region selected from the group consisting of the amino acid sequences of SEQ ID NOs: 31, 33, 35, 37, and 39 or variants of said sequences.

In a preferred embodiment, the heavy chain variable region is SEQ ID NO: 32 or a variant thereof; the light chain variable region is SEQ ID NO: 31 or a variant thereof.

In another preferred embodiment, the heavy chain variable region is SEQ ID NO: 34 or a variant thereof; the light chain variable region is SEQ ID NO: 33 or a variant thereof.

In yet another preferred embodiment, the heavy chain variable region is SEQ ID NO: 36 or a variant thereof; the variable region of the light chain is SEQ ID NO: 35 or a variant thereof.

In yet another preferred embodiment, the heavy chain variable region is SEQ ID NO: 38 or a variant thereof; the light chain variable region is SEQ ID NO: 37 or a variant thereof.

In yet another preferred embodiment, the heavy chain variable region is SEQ ID NO: 40 or a variant thereof; the variable region of the light chain is SEQ ID NO: 39 or a variant thereof.

The antibody or the functional fragment thereof can be a chimeric antibody, a humanized antibody, or a fully human antibody.

The present antibody or functional fragment thereof can be humanized. The preparation of humanized antibody is well known to those skilled in the art. For example, the CDR sequences of the present invention can be transferred into a human antibody variable region to prepare the humanized anti-PCSK9 antibody of the invention. The humanized antibody will not generate anti-antibody reaction (AAR) or human anti-mouse antibody reaction (HAMA), will not be quickly removed by the neutralization of anti-antibody, and will exert an immune effector function.

In some preferred embodiments, the humanized anti-PCSK9 antibody or the functional fragment thereof comprises a heavy chain variable region selected from the group consisting of the amino acid sequences of SEQ ID NOs: 32, 34, 36, 38, and 40 or variants of any of said sequences, and/or light chain variable region selected from the group consisting of the amino acid sequences of SEQ ID NOs: 31, 33, 35, 37, and 39 or variants of said sequences.

In one preferred embodiment of the present humanized antibody or the functional fragment thereof, the heavy chain variable region is SEQ ID NO: 32 or a variant thereof and said light chain variable region is SEQ ID NO: 31 or a variant thereof.

In another preferred embodiment of the present humanized antibody or the functional fragment thereof, the heavy chain variable region is SEQ ID NO: 34 or a variant thereof and the light chain variable region is SEQ ID NO: 33 or a variant thereof.

In another preferred embodiment of the present humanized antibody or the functional fragment thereof, the heavy chain variable region is SEQ ID NO: 36 or a variant thereof and the light chain variable region is SEQ ID NO: 35 or a variant thereof.

In another preferred embodiment of the present humanized antibody or the functional fragment thereof, the heavy chain variable region is SEQ ID NO:38 or a variant thereof and the light chain variable region is SEQ ID NO: 37 or a variant thereof.

In another preferred embodiment of the present humanized antibody or the functional fragment thereof, the heavy chain variable region is SEQ ID NO: 40 or a variant thereof and the light chain variable region is SEQ ID NO: 39 or a variant thereof.

In another preferred embodiment of the present humanized antibody or the functional fragment thereof, the heavy chain variable region is SEQ ID NO: 47 or a variant thereof and the light chain variable region is SEQ ID NO: 45 or a variant thereof.

In another preferred embodiment of the present humanized antibody or the functional fragment thereof, the heavy chain variable region is SEQ ID NO: 49 or a variant thereof and the light chain variable region is SEQ ID NO: 45 or a variant thereof.

The invention also provides an isolated nucleic acid molecule encoding the antibody of the invention or a functional fragment thereof. In a preferred embodiment, the nucleic acid molecule comprises the nucleotide sequence of SEQ ID NOs: 48, 50 and/or 46; or a combination thereof.

The invention further provides an expression vector comprising the nucleic acid molecule and a host cell comprising the expression vector.

The invention provides a method for producing an anti-PCSK9 antibody or a functional fragment thereof, comprising the steps of: culturing the host cell of the invention under the condition allowing the antibody or the functional fragment thereof to be generated, and recovering the generated antibody or functional fragment thereof.

In another aspect, the present invention relates to an immunoconjugate comprising an antibody or a functional fragment thereof conjugated to a therapeutic agent. The therapeutic agent is preferably a toxin, a radioactive isotope, a drug or a cytotoxic agent.

The present invention also relates to a pharmaceutical composition comprising the antibody of the invention or a functional fragment thereof and a pharmaceutically acceptable carrier.

In another aspect, the present invention provides method for preventing or treating diseases or conditions by eliminating, inhibiting or reducing PCSK9 activity, comprising administering to the subject in need of a therapeutically effective amount of the antibody or a functional fragment thereof, the nucleic acid, the expression vector, the host cell, the immunoconjugate or the pharmaceutical composition of the present invention.

The present invention also provides use of the antibody or a functional fragment thereof, the nucleic acid, the expression vector, the host cell, the immunoconjugate or the pharmaceutical composition of the present invention in preparation of medicament for treating diseases or conditions.

The following examples are provided to demonstrate and further explain some preferred embodiments and aspects of the invention, which should not be interpreted as limiting the scope thereof.

EXAMPLES

Example 1: Cloning of Human PCSK9 Extracellular Region and LDLR Extracellular Region into an Eukaryotic Expression System Human PCSK9 extracellular fragment was PCR amplified by using human PCSK9 gene cDNA (from Beijing Sino Biological Inc.) of known sequence as a template (template sequence as follows), with an upstream primer 5'-GTACACTAGTCACCATGGGCACCGTCAGCTC-3' (SEQ ID NO: 52), and a downstream primer 5'-GATCCTCGAGCCTGGAGCTCCTGGGAGG-3' (SEQ ID NO: 53). The amplified product was subjected to speI and XhoI double-enzyme digestion, and cloned into a self-constructed eukaryotic expression plasmid system (pSec CAGA2 ECD). A 293E cell was transfected with the plasmid through PEI. After 6 days, the supernatant of the culture medium was collected and human PCSK9 extracellular region protein was purified via affinity chromatography.

Similarly, LDLR extracellular fragment was PCR amplified by using an upstream primer 5'-GTACGCTAGCCACCATGGGGCCCTGGGGCTG-3' (SEQ ID NO: 43) and a downstream primer 5'-GATCCTCGAGCCCTCACGCTACTGG-3' (SEQ ID NO: 44). The amplified product was subjected to NheI and XhoI double-enzyme digestion, and cloned into a self-constructed eukaryotic expression plasmid system. A 293E cell was transfected with the plasmid through PEI. After 6 days, the supernatant of the culture medium was collected and the LDLR extracellular region was purified.

As shown in FIG. 1 is the SDS-PAGE electrophoresis diagram of human PCSK9 extracellular region protein.

```
Nucleotide sequence of extracellular region of human PCSK9:
                                                          SEQ ID NO: 41
ATGGGCACCG TCAGCTCCAG GCGGTCCTGG TGGCCGCTGC CACTGCTGCT GCTGCTGCTG    61

CTGCTCCTGG GTCCCGCGGG CGCCCGTGCG CAGGAGGACG AGGACGGCGA CTACGAGGAG   121

CTGGTGCTAG CCTTGCGTTC CGAGGAGGAC GGCCTGGCCG AAGCACCCGA GCACGGAACC   181

ACAGCCACCT TCCACCGCTG CGCCAAGGAT CCGTGGAGGT TGCCTGGCAC CTACGTGGTG   241

GTGCTGAAGG AGGAGACCCA CCTCTCGCAG TCAGAGCGCA CTGCCCGCCG CCTGCAGGCC   301

CAGGCTGCCC GCCGGGGATA CCTCACCAAG ATCCTGCATG TCTTCCATGG CCTTCTTCCT   361

GGCTTCCTGG TGAAGATGAG TGGCGACCTG CTGGAGCTGG CCTTGAAGTT GCCCCATGTC   421

GACTACATCG AGGAGGACTC CTCTGTCTTT GCCCAGAGCA TCCCGTGGAA CCTGGAGCGG   481

ATTACCCCTC CACGGTACCG GGCGGATGAA TACCAGCCCC CCGACGGAGG CAGCCTGGTG   541

GAGGTGTATC TCCTAGACAC CAGCATACAG AGTGACCACC GGGAAATCGA GGGCAGGGTC   601

ATGGTCACCG ACTTCGAGAA TGTGCCCGAG GAGGACGGGA CCCGCTTCCA CAGACAGGCC   661

AGCAAGTGTG ACAGTCATGG CACCCACCTG GCAGGGGTGG TCAGCGGCCG GGATGCCGGC   721

GTGGCCAAGG GTGCCAGCAT GCGCAGCCTG CGCGTGCTCA ACTGCCAAGG GAAGGGCACG   781

GTTAGCGGCA CCCTCATAGG CCTGGAGTTT ATTCGGAAAA GCCAGCTGGT CCAGCCTGTG   841

GGGCCACTGG TGGTGCTGCT GCCCCTGGCG GGTGGGTACA GCCGCGTCCT CAACGCCGCC   901

TGCCAGCGCC TGGCGAGGGC TGGGGTCGTG CTGGTCACCG CTGCCGGCAA CTTCCGGGAC   961

GATGCCTGCC TCTACTCCCC AGCCTCAGCT CCCGAGGTCA TCACAGTTGG GGCCACCAAT  1021

GCCCAGGACC AGCCGGTGAC CCTGGGGACT TTGGGGACCA ACTTTGGCCG CTGTGTGGAC  1081

CTCTTTGCCC CAGGGGAGGA CATCATTGGT GCCTCCAGCG ACTGCAGCAC CTGCTTTGTG  1141

TCACAGAGTG GGACATCACA GGCTGCTGCC CACGTGGCTG GCATTGCAGC CATGATGCTG  1201

TCTGCCGAGC CGGAGCTCAC CCTGGCCGAG TTGAGGCAGA GACTGATCCA CTTCTCTGCC  1261

AAAGATGTCA TCAATGAGGC CTGGTTCCCT GAGGACCAGC GGGTACTGAC CCCCAACCTG  1321

GTGGCCGCCC TGCCCCCCAG CACCCATGGG CAGGTTGGC AGCTGTTTTG CAGGACTGTG  1381

TGGTCAGCAC ACTCGGGGCC TACACGGATG CCACAGCCA TCGCCCGCTG CGCCCCAGAT  1441

GAGGAGCTGC TGAGCTGCTC CAGTTTCTCC AGGAGTGGGA AGCGGCGGG CGAGCGCATG  1501

GAGGCCCAAG GGGGCAAGCT GGTCTGCCGG GCCCACAACG CTTTTGGGGG TGAGGGTGTC  1561
```

```
TACGCCATTG CCAGGTGCTG CCTGCTACCC CAGGCCAACT GCAGCGTCCA CACAGCTCCA   1621

CCAGCTGAGG CCAGCATGGG GACCCGTGTC CACTGCCACC AACAGGGCCA CGTCCTCACA   1681

GGCTGCAGCT CCCACTGGGA GGTGGAGGAC CTTGGCACCC ACAAGCCGCC TGTGCTGAGG   1741

CCACGAGGTC AGCCCAACCA GTGCGTGGGC CACAGGGAGG CCAGCATCCA CGCTTCCTGC   1801

TGCCATGCCC CAGGTCTGGA ATGCAAAGTC AAGGAGCATG GAATCCCGGC CCCTCAGGAG   1861

CAGGTGACCG TGGCCTGCGA GGAGGGCTGG ACCCTGACTG GCTGCAGTGC CCTCCCTGGG   1921

ACCTCCCACG TCCTGGGGGC CTACGCCGTA GACAACACGT GTGTAGTCAG GAGCCGGGAC   1981

GTCAGCACTA CAGGCAGCAC CAGCGAAGAG GCCGTGACAG CCGTTGCCAT CTGCTGCCGG   2041

AGCCGGCACC TGGCGCAGGC CTCCCAGGAG CTCCAGTGA
```

Nucleotide sequence of the LDLR extracellular region:
SEQ ID NO: 42

```
ATGGGGCCCT GGGGCTGGAA ATTGCGCTGG ACCGTCGCCT TGCTCCTCGC CGCGGCGGGG

ACTGCAGTGG GCGACAGATG CGAAAGAAAC GAGTTCCAGT GCCAAGACGG GAAATGCATC    121

TCCTACAAGT GGGTCTGCGA TGGCAGCGCT GAGTGCCAGG ATGGCTCTGA TGAGTCCCAG    181

GAGACGTGCT TGTCTGTCAC CTGCAAATCC GGGGACTTCA GCTGTGGGGG CCGTGTCAAC    241

CGCTGCATTC CTCAGTTCTG GAGGTGCGAT GGCCAAGTGG ACTGCGACAA CGGCTCAGAC    301

GAGCAAGGCT GTCCCCCCAA GACGTGCTCC CAGGACGAGT TTCGCTGCCA CGATGGGAAG    361

TGCATCTCTC GGCAGTTCGT CTGTGACTCA GACCGGGACT GCTTGGACGG CTCAGACGAG    421

GCCTCCTGCC CGGTGCTCAC CTGTGGTCCC GCCAGCTTCC AGTGCAACAG CTCCACCTGC    481

ATCCCCCAGC TGTGGGCCTG CGACAACGAC CCCGACTGCG AAGATGGCTC GGATGAGTGG    541

CCGCAGCGCT GTAGGGGTCT TTACGTGTTC CAAGGGGACA GTAGCCCCTG CTCGGCCTTC    601

GAGTTCCACT GCCTAAGTGG CGAGTGCATC CACTCCAGCT GGCGCTGTGA TGGTGGCCCC    661

GACTGCAAGG ACAAATCTGA CGAGGAAAAC TGCGCTGTGG CCACCTGTCG CCCTGACGAA    721

TTCCAGTGCT CTGATGGAAA CTGCATCCAT GGCAGCCGGC AGTGTGACCG GGAATATGAC    781

TGCAAGGACA TGAGCGATGA AGTTGGCTGC GTTAATGTGA CACTCTGCGA GGGACCCAAC    841

AAGTTCAAGT GTCACAGCGG CGAATGCATC ACCCTGGACA AAGTCTGCAA CATGGCTAGA    901

GACTGCCGGG ACTGGTCAGA TGAACCCATC AAAGAGTGCG GGACCAACGA ATGCTTGGAC    961

AACAACGGCG GCTGTTCCCA CGTCTGCAAT GACCTTAAGA TCGGCTACGA GTGCCTGTGC   1021

CCCGACGGCT TCCAGCTGGT GGCCCAGCGA AGATGCGAAG ATATCGATGA GTGTCAGGAT   1081

CCCGACACCT GCAGCCAGCT CTGCGTGAAC CTGGAGGGTG GCTACAAGTG CCAGTGTGAG   1141

GAAGGCTTCC AGCTGGACCC CCACACGAAG GCCTGCAAGG CTGTGGGCTC CATCGCCTAC   1201

CTCTTCTTCA CCAACCGGCA CGAGGTCAGG AAGATGACGC TGGACCGGAG CGAGTACACC   1261

AGCCTCATCC CCAACCTGAG GAACGTGGTC GCTCTGGACA CGGAGGTGGC CAGCAATAGA   1321

ATCTACTGGT CTGACCTGTC CCAGAGAATG ATCTGCAGCA CCCAGCTTGA CAGAGCCCAC   1381

GGCGTCTCTT CCTATGACAC CGTCATCAGC AGGGACATCC AGGCCCCCGA CGGGCTGGCT   1441

GTGGACTGGA TCCACAGCAA CATCTACTGG ACCGACTCTG TCCTGGGCAC TGTCTCTGTT   1501

GCGGATACCA AGGGCGTGAA GAGGAAAACG TTATTCAGGG AGAACGGCTC CAAGCCAAGG   1561

GCCATCGTGG TGGATCCTGT TCATGGCTTC ATGTACTGGA CTGACTGGGG AACTCCTGCC   1621

AAGATCAAGA AAGGGGGCCT GAATGGTGTG GACATCTACT CGCTGGTGAC TGAAAACATT   1681

CAGTGGCCCA ATGGCATCAC CCTAGATCTC CTCAGTGGCC GCCTCTACTG GGTTGACTCC   1741

AAACTTCACT CCATCTCAAG CATCGATGTC AACGGGGGCA ACCGGAAGAC CATCTTGGAG   1801

GATGAAAAGA GGCTGGCCCA CCCCTTCTCC TTGGCCGTCT TTGAGGACAA AGTATTTTGG   1861
```

```
ACAGATATCA TCAACGAAGC CATTTTCAGT GCCAACCGCC TCACAGGTTC CGATGTCAAC 1921

TTGTTGGCTG AAAACCTACT GTCCCCAGAG GATATGGTTC TCTTCCACAA CCTCACCCAG 1981

CCAAGAGGAG TGAACTGGTG TGAGAGGACC ACCCTGAGCA ATGGCGGCTG CCAGTATCTG 2041

TGCCTCCCTG CCCCGCAGAT CAACCCCCAC TCGCCCAAGT TTACCTGCGC CTGCCCGGAC 2101

GGCATGCTGC TGGCCAGGGA CATGAGGAGC TGCCTCACAG AGGCTGAGGC TGCAGTGGCC 2161

ACCCAGGAGA CATCCACCGT CAGGCTAAAG GTCAGCTCCA CAGCCGTAAG GACACAGCAC 2221

ACAACCACCC GACCTGTTCC CGACACCTCC CGGCTGCCTG GGGCCACCCC TGGGCTCACC 2281

ACGGTGGAGA TAGTGACAAT GTCTCACCAA GCTCTGGGCG ACGTTGCTGG CAGAGGAAAT 2341

GAGAAGAAGC CCAGTAGCGT GAGGG
```

Example 2: ELISA Assay for the Binding of Human PCSK9 Recombinant Protein to LDLR 2.1 Biotin-Labeling of Human PCSK9 Recombinant Protein Human PCSK9 recombinant protein and biotin-xx-NHS dissolved in DMSO were mixed at a ratio of 1:10, kept at room temperature for 2 hrs, and then the reactant mixture was passed through a 10 kD ultrafiltration column to separate biotin-labeled human PCSK9 and free biotin.

2.2 ELISA Detection for the Binding of Human PCSK9 and LDLR

In order to determining the binding ability of human PCSK9 with LDLR, 1 μg/ml of LDLR was plated on the 96-well ELISA plate in coating buffer, stored at 4° C. overnight. The next day, the solution in the wells was discarded, and the wells were washed with a washing buffer for three times. Then, PBS solution containing 2% of milk was added for blocking for 60 minutes. After washing with washing buffer for three times, 100 μl of biotin-labeled human PCSK9 at different concentrations was added, incubated for 1 hour at room temperature, washed with washing buffer for three times. HRP cross-linked goat anti-mouse antibody was diluted at 1:10000 with washing buffer, incubated for 1 hour at room temperature, washed with washing buffer for three times, and a 50 μl TMB substrate solution was added for developing. After reacting for 8 minutes at room temperature, the reaction was terminated by 100 μl 12M HCl solution, and the absorbance was read at 450 nm.

Figure 2:
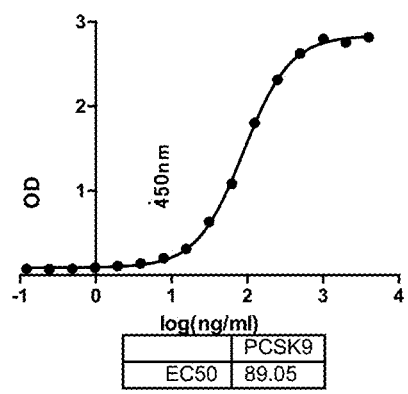
FIG. 2: Elisa assay of the binding of human PCSK9 with LDLR.

As can be seen from FIG. 2, human PCSK9 recombinant protein can specifically bind to LDLR in a dose-dependent fashion.

Example 3: Cell-Level Assay for the Binding of PCSK9 to LDLR 3.1 Construction of 293F-LDLR Stably Transfected Cell Strain The constructed eukaryotic expression plasmid with the full-length LDLR sequence with puromycin screening system was transfected into 293F adherent cells through PEI. 24 hours after transfection, screening was carried out with purmycin (2 μg/mL) until a 293F-LDLR stably transfected cell pool was formed. Meanwhile, a 96-well plate was plated at 0.8 cells/well in limiting dilution. After 15 days, 293F-LDLR monoclonal antibody was picked out and passaged to form a 293F-LDLR stably transfected cell strain.

3.2 the Binding of Biotin-Labeled Human PCSK9 D347Y with 293F-LDLR Stably Transfected Cell Strain Different concentrations of biotin-labeled human PCSK9 D347Y recombinant protein was mixed with 293F-LDLR stably transfected cell line, incubated for 15 minutes at a temperature of 4° C. After washing for 3 times with FACS buffer (20 mM Tris, 100 mM NaCl, 2 mM $Ca^{2+}$, 1% FBS, pH7.4), straptavidin allophycocyanin(SA-APC, 2 μg/mL) was added, and incubated for 20 min at 4° C. After washing with FACS buffer for three times, detection was carried out by flow cytometry.

Figure 3:
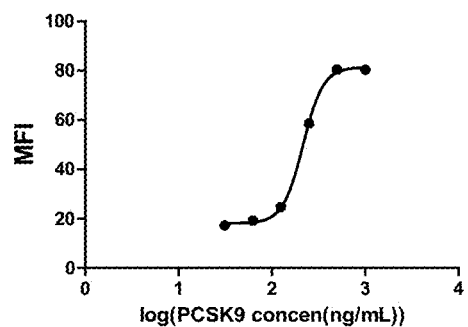
FIG. 3: FACS detection of the binding of human PCSK9 with LDLR.

As shown in FIG. 3, the constructed human PCSK9 D347Y recombinant protein can specifically bind to LDLR on 293T-LDLR cells, showing a dose dependent effect.

3.3 the Binding of Biotin-Labeled Human PCSK9 to LDLR on HepG2 Cells

To further verifying the binding ability of hPCSK9 with LDLR, different concentrations of biotin-labeled human PCSK9 D347Y recombinant protein was mixed with HepG2 cells, incubated for 15 minutes at a temperature of 4° C. After washing for 3 times with PBS, straptavidin allophycocyanin(SA-APC, 2 μg/mL) was added, and incubated for 20 min at 4° C. After washing with FACS buffer for three times, detection was carried out by flow cytometry.

Figure 4:
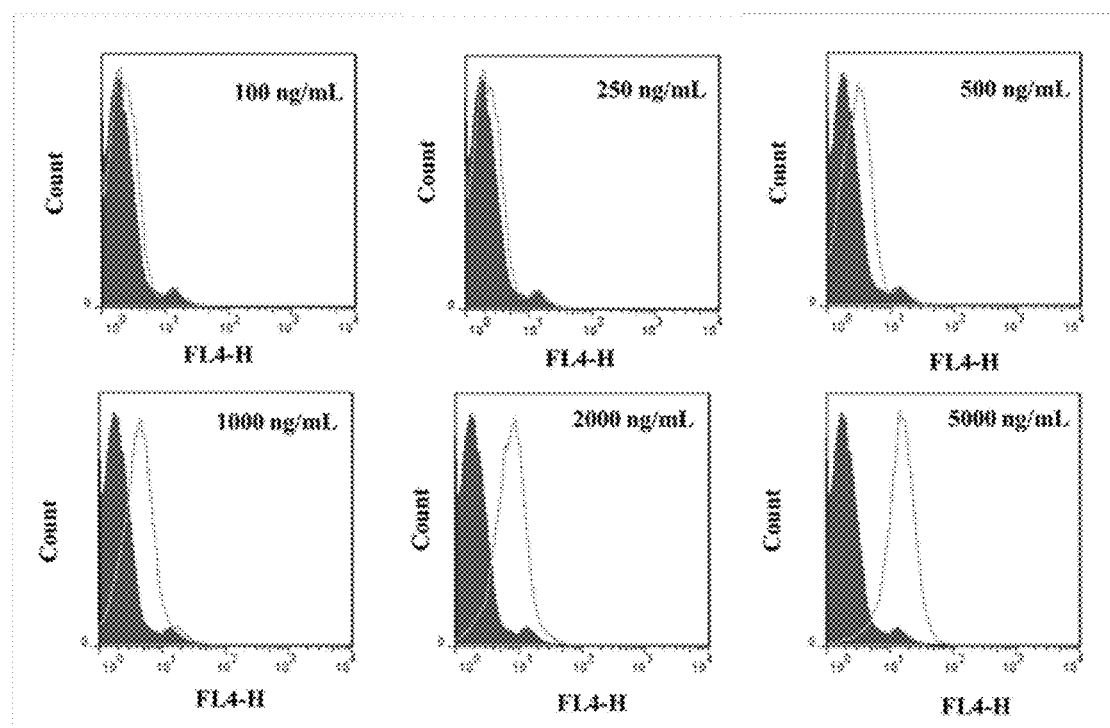
FIG. 4: FACS verification of the binding of human PCSK9 with LDLR.

As shown in FIG. 4, the result is consistent with the above. Human PCSK9 recombinant protein can specifically bind to LDLR on HepG2 cells.

Example 4: Preparation of Anti-PCSK9 Murine-Derived Antibody 4.1 Immunizing Animals:

Human PCSK9 recombinant protein as antigen was mixed with an equal amount of immune adjuvant (Freund's adjuvant), and 5 six-week old female FVB mice were immunized. After the first immunization, the immunization was boosted once every week, with total 4 immunizations.

4.2 Cell Fusion

After the last boost immunization, lymph nodes at the base of mouse thigh were collected, and grinded in normal saline, and the suspension rich of lymphocytes were collected, fused with SP20 cells according to a conventional electrotransfection method. The fused cells were distributed in 96 wells with RPMI-1640 complete culture medium containing HAT, and cultured at 37° C. with 5% $CO_2$.

Example 5: Ligand and Receptor Blocking Assay 1220 clones that can secrete antibodies binding to human PCSK9 protein were screened out among 20000 different monoclonal hybridoma cells via ELISA reaction. 15 out of these 1220 antibodies can inhibit the binding of biotin-labeled human PCSK9 with LDLR on the HepG2. We focused on sequential experiments on the ones with inhibitory ability in the top 5.

The supernatant of the above five hybridoma cells were mixed with biotin-labeled human PCSK9 (400 ng/ml), and incubated at room temperature for 20 min. Then, the mixture and 293T-LDLR stably transfected cell strain were incubated at 37° C. for 15 minutes. After washing with PBS for 3 times, 0.2 μg/ml SA-APC was added and incubated at 4° C. for 15 minutes. After washing with PBS for 3 times, flow cytometer was used to verify if the antibody secreted by the hybridoma cell can inhibit the binding of human PCSK9 with LDLR on the surface of the 293F-LDLR cells. Similarly, using reference antibody anti-PCSK9 monoclonal antibody (Merck) as control, the above assay was performed at a concentration of 4 μg/ml.

Figure 5:
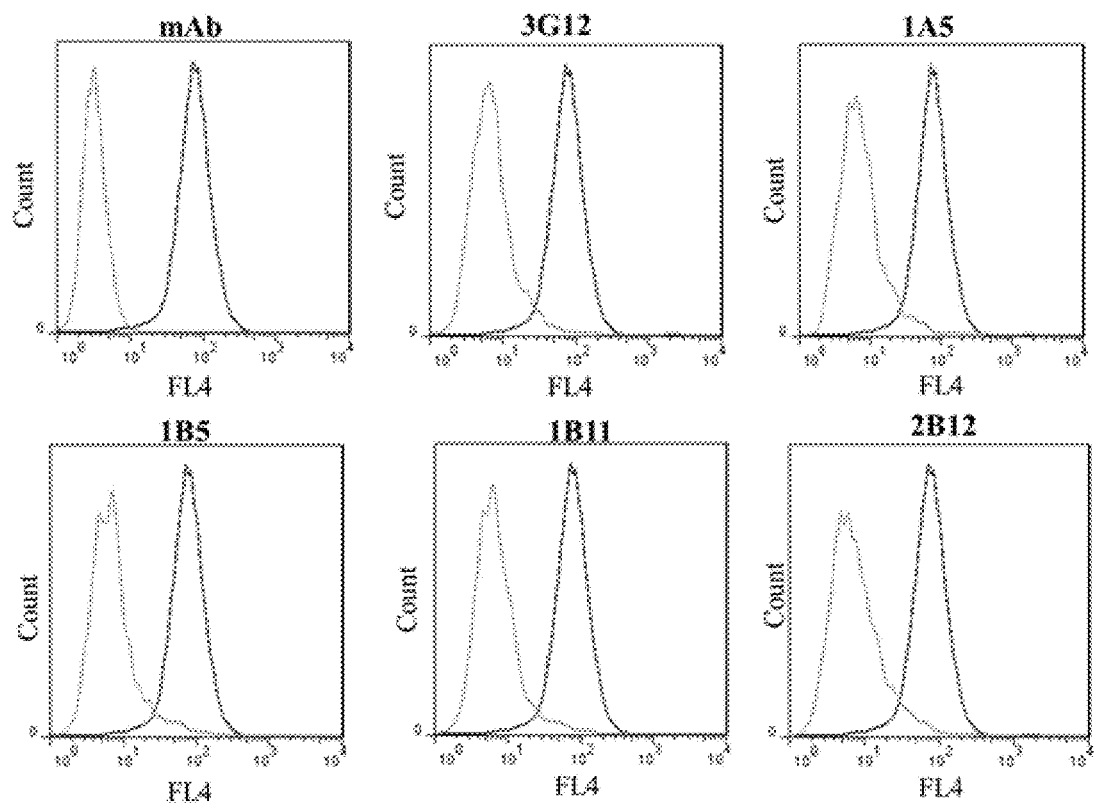
FIG. 5: FACS detection of the binding of candidate hybridoma cells with human PCSK9.

As shown in FIG. 5, the flow cytometry result shows that consistent with the reference antibody, the 5 candidate monoclonal antibodies 3G12, 1A5, 1B5, 1B11 and 2B12 all can be effectively bind with human PCSK9, so as to inhibit the degradation of LDLR.

Example 6: Cross Reaction Between PCSKs Among Different Species

Cross-reaction among monoclonal murine-derived candidate antibodies 3G12, 1A5 and 1B5, 1B11 and 2B12; human-derived PCSK9; murine-derived PCSK9, and Cynomolgus monkey-derived PCSK9 were detected with ELISA assay. The experimental results show that the anti-PCSK9 murine-derived antibody prepared by us can cross react with anti-PCSK9 antibodies reported by other companies, which will facilitate animal experiments and save time consumption. The experimental results are shown in table 1:

TABLE 1

| Sample | 3G12 | 1A5 | 1B5 | 1B11 | 2B12 |
| --- | --- | --- | --- | --- | --- |
| Species cross-reactivity | h/m/cy | h/m/cy | h/m/cy | h/cy | h/m/cy |

H: human-derived; m: murine-derived; cy: Cynomolgus monkey-derived.

Example 7: Determining the Binding Constant with Human PCSK9 Recombinant Protein As shown in table 2, the combination constant between different murine-derived antibodies and HPCSK9 was determined with a ForteBio instrument, indicating that the prepared murine-derived antibody can specifically bind to human PCSK9.

TABLE 2

| Sample | 3G12 | 1A5 | 1B5 | 1B11 | 2B12 |
| --- | --- | --- | --- | --- | --- |
| KD (nM) | 0.28 | 0.91 | 0.90 | 4.7 | 0.49 |

Example 8: Binding of Murine-Derived Candidate Antibody with Human PCSK9

A 96-well Elisa plate was plated, coated with 4 μg/ml streptavidin, incubated at 37° C. for 90 min. Then the solution in the wells was discarded, and the wells were washed with washing buffer for three times, and a PBS solution containing 2% of milk was added for blocking for 60 minutes. After washing with washing buffer for three times, each well was added with 2 μg/ml biotin-labeled human PCSK9, incubated for 1 hour at 37° C., and washed with washing buffer for three times. Then chimeric antibody at different dilution ratios was added and incubated for 1 hour at 37° C. After washing with washing buffer for three times, the HPR-labeled mouse anti-human IgG (H+L) was diluted with washing buffer at 1:5000, incubated at room temperature for 1 hour. After washing with washing buffer for three times, 100 μl TMB substrate solution was added for developing, reacting for 10 minutes at room temperature. The reaction was terminated by 100 μl 12M HCl solution and the absorbance was read out at 450 nm.

Figure 6:
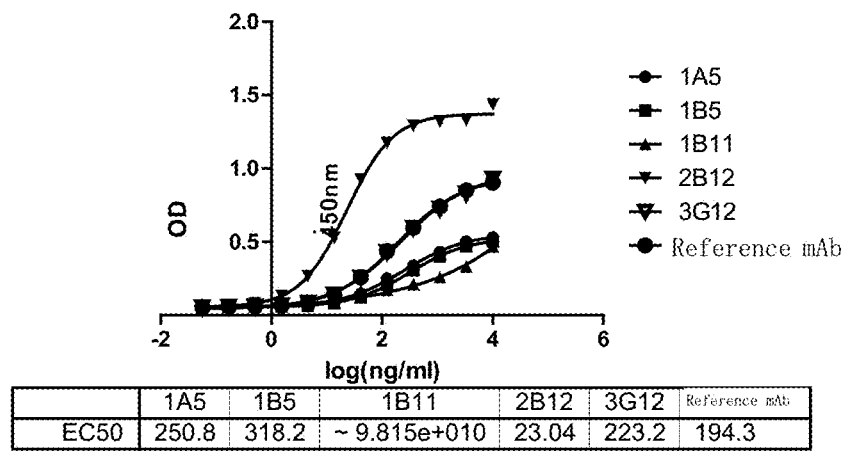
FIG. 6: Assay for the binding of murine-derived antibody and PCSK9 D347Y (antigen-coated)

As shown in FIG. 6, the murine-derived antibody can specifically bind to human PCSK9. Compared with the reference antibody, 2B12 and 3G12 have better binding ability.

Figure 7:
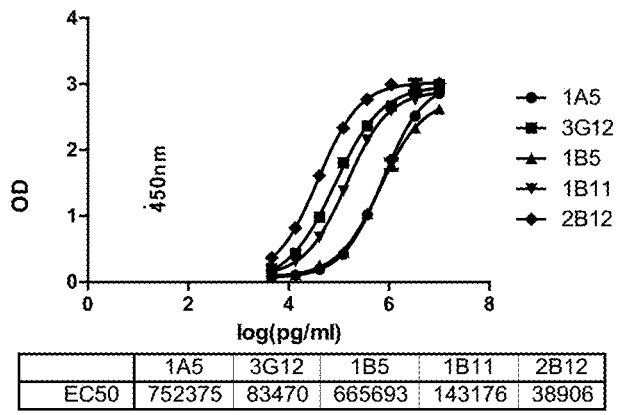
FIG. 7: Assay for the binding of murine-derived antibody and PCSK9 D347Y (antibody-coated)
Figure 8:
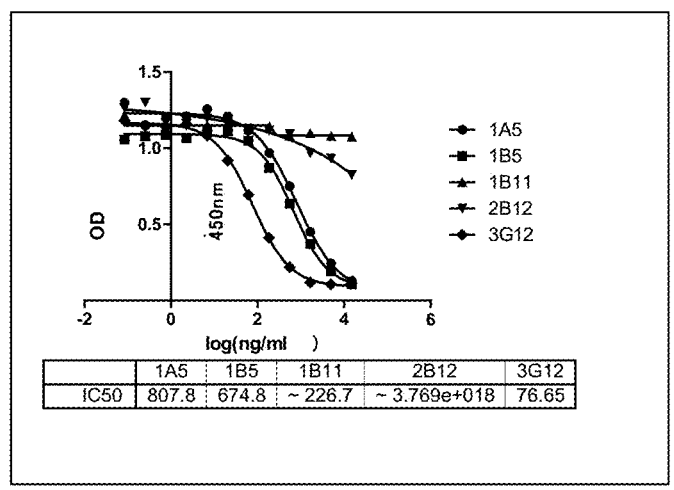
FIG. 8: Assay for the competitive binding of murine-derived antibody with PCSK D347Y antigen epitope against reference antibody.

In order to further verify the specific binding of the antibody with human PCSK9, similar to the above experiment, the antibody (1 μg/ml) was plated in a 96 well plate, incubated for 60 minutes at 37° C. Then the solution in the wells was discarded, and the wells were washed with washing buffer for three times. Then, the PBS solution containing 2% of milk was added for blocking for 60 minutes. After washing with washing buffer for three times, 100 μl biotin-labeled PCSK9 at different concentrations was added, incubated at 37° C. for 1 hour. After washing with washing buffer for 3 times, HRP-strep was diluted with washing buffer at ratio of 1:5000, incubated for 1 hour at room temperature. After washing with washing buffer for 3 times, 100 μl TMB substrate solution was added for developing, and reacted for 10 minutes at room temperature. The reaction was terminated by 100 μl 12M HCl solution and the absorbance was read out at 450 nm. As shown in FIG. 7, the binding profile of murine-derived antibody with human PCSK9 is consistent with that in the previous experiment.

On this basis, the similarities and differences among the binding of different murine-derived antibodies with human PCSK9 antigen epitopes were further designed and compared: Coating with 4 μg/ml streptavidin and incubating at a constant temperature of 37° C. for 90 minutes. Then the solution in the wells was discarded, and the wells were washed with washing buffer for three times. Then, the PBS solution containing 2% of milk was added for blocking for 60 minutes. After washing with washing buffer for three times, 100 μl biotin-labeled PCSK9 at 2 μg/ml was added to each well, incubated at 37° C. for 1 hour, and washed with washing buffer for 3 times. Then, chimeric antibodies that were diluted at different dilution ratios with 200 ng/ml reference antibody were added, incubated at 37° C. for 90 min. After washing with washing buffer for 3 times, HRP-labeled goat anti-human IgG-Fc was diluted with washing buffer at a ratio of 1:5000, incubated for 1 hour at room temperature. After washing 3 times with washing buffer, 100μl TMB substrate solution was added for developing, and reacted for 10 minutes at room temperature. The reaction was terminated by 100 μl 12M HCl solution and the absorbance was read out at 450 nm.

As shown in FIG. 8, 1B11 and 2B12 cannot significantly compete with the reference antibody for binding to the human PCSK9 antigen epitope; while 1A5 and 1B5, 3G12 can significantly competitively bind to the antigen epitopes on human PCSK that would otherwise be bound by the reference monoclonal antibody. It is suggested that the competitive binding ability of 1A5, 1B5 and 3G12 is significantly stronger than that of a reference antibody.

Example 9: Effect on the LDL Uptake of HepG2 Cells

Antibodies at different dilution ratios were incubated with biotin-labeled human PCSK9-D347Y (2.5 μg/mL) for 1 hour at room temperature, and then mixed with FL-LDL (5 μg/mL), incubated for 3 hours at 37° C., and washed for three times with PBS, and then fluorescence detection was carried out with Tecan Safire 2 (Ex 514 nm/Em 570 nm).

Figure 9:
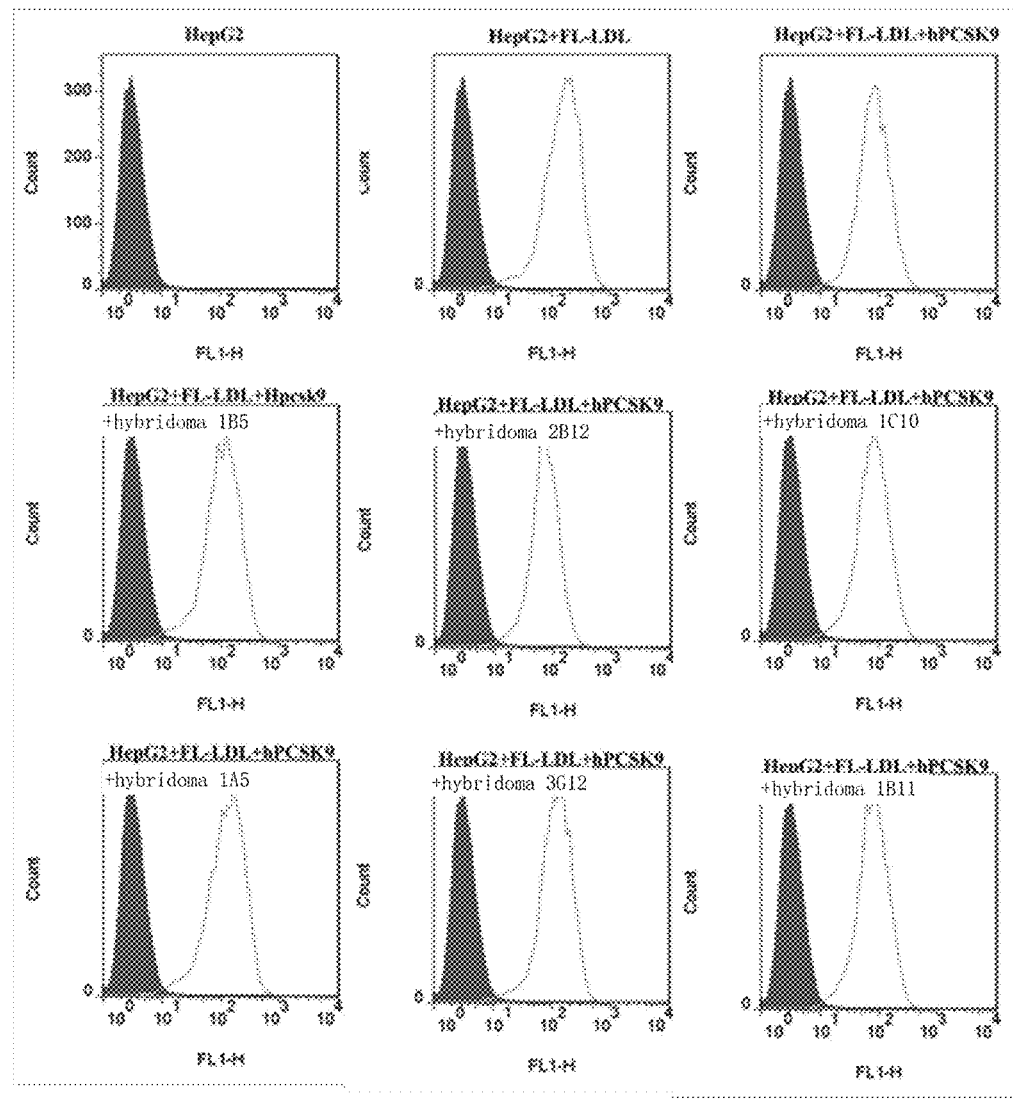
FIG. 9: Influence of murine-derived antibody on HepG2 cell LDL uptake.

As can be seen from the results of FIG. 9 and Table 3, different murine-derived monoclonal antibodies can bind to human PSCK9 to inhibit its effect on the LDL uptake with an IC50 of about 1 μg/ml.

TABLE 3

| Sample | 3G12 | Reference antibody |
|---|---|---|
| IC50(nM) | 5.5 | 5.9 |

Example 10: Obtaining the Candidate Variable Region Sequences

The candidate hybridoma cells were cultured, centrifuged at 1000 rpm, and the total RNA was extracted by trizol. After being synthesized, the first cDNA strand was used as subsequent template to amplify the corresponding variable region DNA sequence of the hybridoma cells (Jones and Bendig 1991). In 50 μl reaction system, 1 μl cDNA, 10×PCR buffer 5 μl, upper- and down-stream primers 1 μl respectively (25 pmol), dNTP 1 μl, 25 mmol PL MgCl2 1 μl, H2O 39 μl were added respectively, 95° C. pre-denaturing for 10 min, and Taq enzyme 1 μl was added. Temperature cycles and PCR amplification were carried out. The reaction conditions were 94° C. denaturation for 1 min, 58° C. annealing for 1 min, 72° C. extending for 15 s, in total 32 cycles, and then kept at 72° C. for 10 min.

After sequencing the amplified products, the heavy chain and light chain variable region sequences in the candidate hybridoma are:

```
1A5 LC
SEQ ID NO: 31
DIQMTQSPSSLSASLGDKVTITCKASQDINKYIDWYQHKPGKGPRLLIHYTSTLQPGIPS
RFSGSGSGRDYSFSISNLEPEDIATYYCVQYDDLWTFGGGTKLEIK

SEQ ID NO: 1 LCDR1:
ASQDINKYID

SEQ ID NO: 2 LCDR2:
YTSTLQP

SEQ ID NO: 3 LCDR3:
VQYDDLWT

1A5 HC
SEQ ID NO: 32
QVQLKQSGPSLVQPSQSLSITCTVSGFSLTSYGVHWVRQSPGKGLEWLGVIWRGGSTD
YNAAFMSRLSITKDNSKSQVFFKMNSLQADDTAIYYCANHRDWGQGTLVTVSA

SEQ ID NO: 4 HCDR1:
SYGVH

SEQ ID NO: 5 HCDR2:
VIWRGGSTDYNAAFMS

SEQ ID NO: 6 HCDR3:
HRD

3G12 LC
SEQ ID NO: 33
DIQMTQSPSSLSASLGGKVTITCKASQDINKYIDWYQHKPGKSPRLLIHYASTLQPGIPS
RFSGSGSGRDYSFSISNLEPEDIATYYCLQYDDLWTFGGGTKLEIK

SEQ ID NO: 7 LCDR1:
ASQDINKYID

SEQ ID NO: 8 LCDR2:
YASTLQP

SEQ ID NO: 9 LCDR3:
LQYDDLWT

3G12 HC
SEQ ID NO: 34
QVQLKQSGPSLLQPSQSLSITCTVSGFSLTSYGIHWVRQSPGKGLEWLGVIWRGGITDY
NAPFMSRLNITKDNSKNQVFFKMNSLQVDDTAIYYCANHRDWGQGTLVTVSA

SEQ ID NO: 10 HCDR1:
SYGIH

SEQ ID NO: 11 HCDR2:
VIWRGGITDYNAPFMS

SEQ ID NO: 12 HCDR3:
HRD

1B5 LC
SEQ ID NO: 35
DIVLTQSPASLVVSLGQRATISCRASESVDNYGISFMNWFQQKPGQPPKWYTTSNQGS
GVRARLSGSGCGTDFSLNIHPMEEDDSAMYFCQQSKEVPYTFGGGTKLEIK
```

-continued

SEQ ID NO: 13 LCDR1:
RASESVDNYGISFMN

SEQ ID NO: 14 LCDR2:
TTSNQGS

SEQ ID NO: 15 LCDR3:
QQSKEVPYT

1B5 HC
SEQ ID NO: 36
DVQLQESGPGLVKPSQSLSLTCTVTGYSITSDYAWNWIRQFPGNKVEWMGYISYSGSS
SYNPSLKGRISITRDTSKNQFFLQLNSVTTEDTATYYCARFYYRFDAYFDSWGQGTTLT
VSS

SEQ ID NO: 16 HCDR1:
SDYAWN

SEQ ID NO: 17 HCDR2:
YISYSGSSSYNPSLKG

SEQ ID NO: 18 HCDR3:
FYYRFDAYFDS

2B12 LC
SEQ ID NO: 37
DIVLTQSPASLAVSLGQRATISCRASESVEYYGTSLMHWYQHKPGQTPKWYSGSNVE
SGVPARFSGSGSGTDFSLNIHPVEEDDIAMYFCQQSREVPSTFGGGTKLEIK

SEQ ID NO: 19 LCDR1:
RASESVEYYGTSLMH

SEQ ID NO: 20 LCDR2:
SGSNVES

SEQ ID NO: 21 LCDR3:
QQSREVPST

2B12 HC
SEQ ID NO: 38
DVQLQESGPGLVKPSQSLSLTCSVTGFSITSDYAWNWIRQFPGNKLEWMGYISYSGTTN
YNPSLKSRISITRDTSKNQFFLHLNSVITEDTATYYCARREGHYSWFPYWGQGTLVTVS
A

SEQ ID NO: 22 HCDR1:
SDYAWN

SEQ ID NO: 23 HCDR2:
YISYSGTTNYNPSLKS

SEQ ID NO: 24 HCDR3:
REGHYSWFPY

1B11 LC
SEQ ID NO: 39
DIQMTQSPASLSASVGETVTITCRASENIYSYLAWYQQKQENSPQLLVYNAYTLADGV
PSRFSGSGSGTQFSLKIISLQPEDFGNYYCQHHYRTPPTFGGGTKLEIK

SEQ ID NO: 25 LCDR1:
RASENIYSYLA

SEQ ID NO: 26 LCDR2:
NAYTLAD

SEQ ID NO: 27 LCDR3:
QHHYRTPPT

1B11 HC
SEQ ID NO: 40
QVQLQQSGAVLVRPGTSIKVSCKASGYAFTNYLIEWIKKRPGQGLEWIGMINPGSGDT
NFNEKFKAKATLTADKSSTTAYMQLNSLTFDDSAVYFCARSSQLGLPYWGQGTLVTV
SA

SEQ ID NO: 28 HCDR1:
NYLIE

SEQ ID NO: 29 HCDR2:
MINPGSGDTNFNEKFKA

SEQ ID NO: 30 HCDR3:
SSQLGLPY

Example 11: Constructing Chimeric Antibody Expression Vector

Heavy chain constant region Fc fragment and light chain k/£ constant region were cloned from human blood cells (Beijing Blood Institute), and then ligated into pCDNA3.1 plasmid for engineering. The above heavy chain and light chain sequence fragments were synthesized by Genscript, with the heavy chain cleaved by BspqI and the light chain by BspqI, ligated into engineered pCDNA3.1 plasmids respectively, and sequenced to obtain correct clones. The sequential experimental materials were obtained by transfecting this series of plasmids into cells and purification. Similar to the above experiments, the heavy chain and light chain were cloned into the engineered pCDNA3.1 plasmid comprising murine heavy chain constant region Fc fragment and light chain k/£ constant region.

Example 12: Binding of Chimeric Antibody with Human PCSK9

A 96-well ELISA plate was plated, coated with 4 µg/ml streptavidin, and incubated at 37° C. for 90 min. Then, the solution inside the wells was discarded, and the wells were washed with washing buffer for three times. PBS solution containing 2% milk was added for blocking for 60 minutes. After washing with washing buffer for three times, 100 µl biotin-labeled PCSK9 at 2 µg/ml was added to each well, incubated at 37° C. for 1 hour, and washed with washing buffer for 3 times. Then, chimeric antibodies that were diluted at different dilution ratio were added, incubated at 37° C. for 1 hour. After washing with washing buffer for 3 times, HRP-labeled mouse anti-human IgG (H+L) was diluted with washing buffer at ratio of 1:5000, incubated for 1 hour at room temperature. After washing for 3 times with washing buffer, 100 µl TMB substrate solution was added for developing, and reacted for 10 minutes at room temperature. The reaction was terminated by 100 µl 12M HCl solution and the absorbance was read out at 450 nm.

Figure 10:
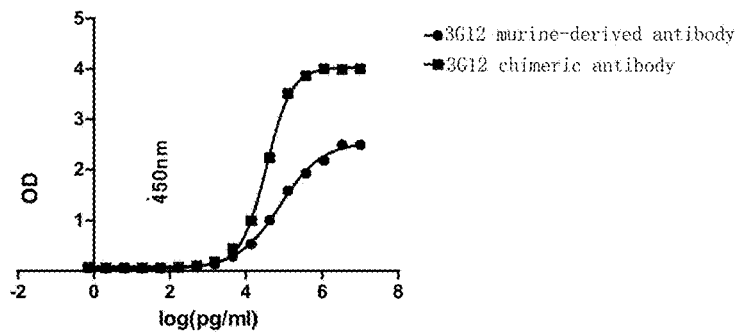
FIG. 10: Binding of chimeric antibody with human PCSK9.

As shown in FIG. 10, 3G12 chimeric antibody and the murine-derived antibody can both specifically bind to human PCSK9.

Example 13: The Effect of Chimeric Antibody on the Cell-Uptake of LDL on HepG2 Cells The constructed chimeric antibody (10 µg/ml) and biotin-labeled human PCSK9(400 ng/ml) were mixed and incubated at room temperature for 60 min. The mixture was added to HepG2 cells, and then FL-LDL(5 µg/ml) were added, incubated at 37° C. for 3 hours. After washing 3 times with PBS, the samples were loaded and detected on flow cytometry.

Figure 11:
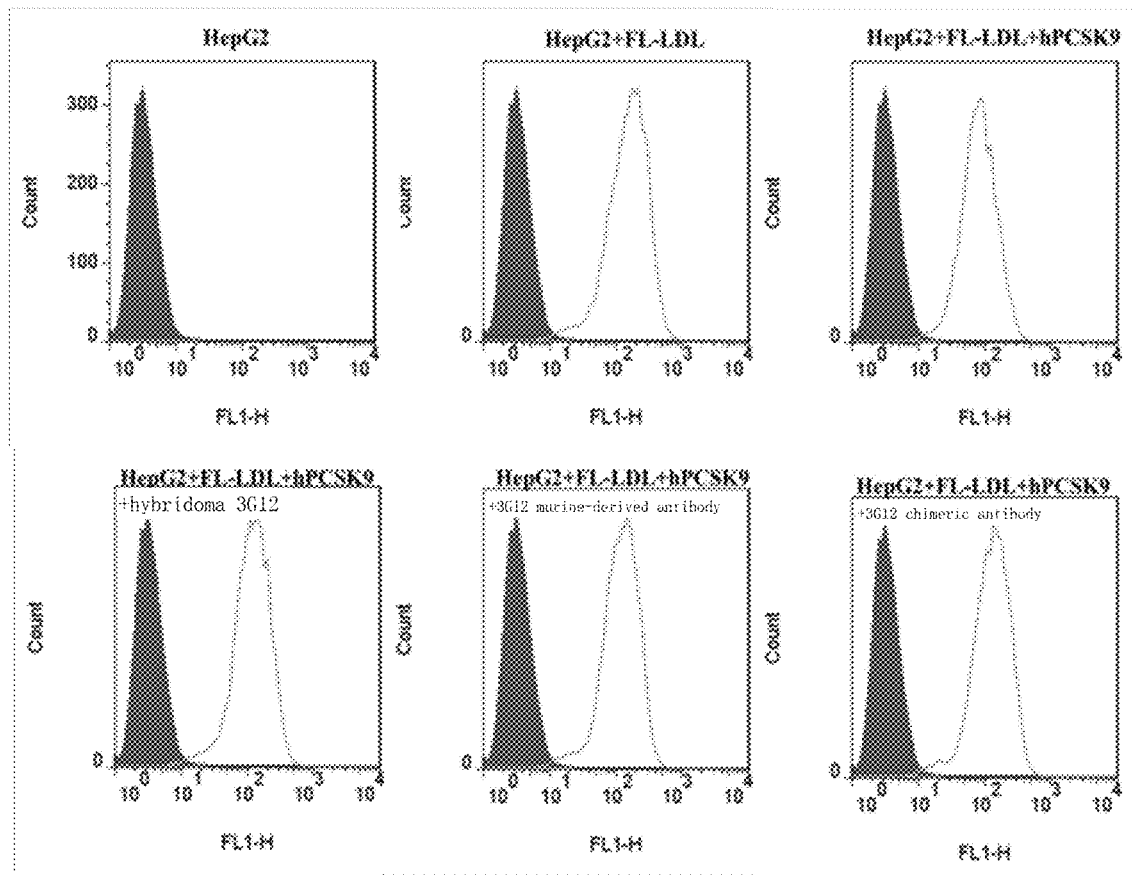
FIG. 11: Effect of chimeric antibody on LDL uptake of HepG2 cells.

As shown in FIG. 11, the constructed 3G12 chimeric antibody can inhibit the effect of human PCSK9 on the LDL uptake.

Example 14: The Humanization of the Antibody

Humanization was carried out according to the variable region sequences of the antibodies secreted by the above obtained hybridoma cells. Briefly, the humanization process involved the following steps: A, aligning the gene sequences of the antibodies secreted by each hybridoma cells with the gene sequence of human embryonic line antibody, and finding out the sequence with high homology; B, analyzing the HLA-DR affinity to select the human embryonic line framework sequence with low affinity; C, utilizing computer simulation technology to speculate the space-3D binding profile by analyzing the variable region and the adjacent frame amino acid sequence by molecular docking. By calculating factors such as electrostatic force, Van der Waals force, hydrophilicity, hydrophobicity, and entropy, analyzing the individual critic amino acids that can interact with PD-1 and maintain the spatial construction in each antibody gene sequence secreted by hybridoma cells, grafting it back to the selected human embryonic line gene framework, and based on such labeling out the framework amino acid sites that need to be kept. Synthesizing random primers and preparing phase library, to screen humanized antibody library (Pini, A. et al. (1998).

Design and Use of a Phage Display Library: HUMAN ANTIBODIES WITH 10 SUBNANOMOLAR AFFINITY AGAINST A MARKER OF ANGIOGENESIS ELUTED FROM A TWO-DIMENSIONAL GEL., Journal of Biological Chemistry, 273(34): 21769-21776). Based on such, we obtained the various following humanized antibodies, including the following clones: 32 and 77, for which they share the same light chain.

```
32/77-LC
(SEQ ID NO: 45, light chain nucleotide sequence)
DIQMTQSPSSLSASVGDRVTITCQQASQDINKYIDWYQHKPGKAPKLLIH

YASTLQPGVPSRFSGSGSGRDYTFTISSLQPEDIATYYCLQYDDLWTFGQ

GTKVEIK (SEQ ID NO: 46, light chain nucleotide sequence)
GACATCCAGATGACCCAGAGCCCCAGCAGCCTGAGCGCCAGCGTGGGCGA

CAGAGTGACCATCACCTGCCAGGCCAGCCAGGACATCAACAAGTACATCG

ACTGGTACCAGCACAAGCCCGGCAAGGCCCCCAAGCTGCTGATCCACTAC

GCCAGCACCCTGCAGCCCGGCGTGCCCAGCAGATTCAGCGGCAGCGGCAG

CGGCAGAGACTACACCTTCACCATCAGCAGCCTGCAGCCCGAGGACATCG

CCACCTACTACTGCCTGCAGTACGACGACCTGTGGACCTTCGGCCAGGGC

ACCAAGGTGGAGATCAAG

32-HC (SEQ ID NO: 47, heavy chain nucleotide
sequence)
QVQLQESGPGLVKPSQTLSLTCTVSGFSISSYGIHWIRQSPGKGLEWIGV

IWRGGITDYNAPFMSRVTISKDNSKNQVSFKLSSVTAADTAVYYCANHRD

WGQGTLVTVSS (SEQ ID NO: 48, heavy chain nucleotide sequence)
CAGGTGCAGCTGCAGGAAAGCGGCCCGGGCCTGGTGAAACCGAGCCAGAC

CCTGAGCCTGACCTGCACCGTGAGCGGCTTTAGCATTAGCAGCTATGGCA

TTCATTGGATTCGCCAGAGCCCGGGCAAAGGCCTGGAATGGATTGGCGTG

ATTTGGCGCGGCGGCATTACCGATTATAACGCGCCGTTTATGAGCCGCGT

GACCATTAGCAAAGATAACAGCAAAAACCAGGTGAGCTTTAAACTGAGCA

GCGTGACCGCGGCGGATACCGCGGTGTATTATTGCGCGAACCATCGCGAT

TGGGGCCAGGGCACCCTGGTGACCGTGAGCAGC

77-HC
(SEQ ID NO: 49, heavy chain nucleotide sequence)
QVQLQESGPGLVKPSQTLSLTCTVSGFSISSYGVHWIRQSPGKGLEWIGV

IWRGGSTDYNAAFMSRVTISKDNSKNQVSFKLSSVTAADTAVYYCANHRD

WGQGTLVTVSS (SEQ ID NO: 50, heavy chain nucleotide sequence)
CAGGTGCAGCTGCAGGAAAGCGGCCCGGGCCTGGTGAAACCGAGCCAGAC

CCTGAGCCTGACCTGCACCGTGAGCGGCTTTAGCATTAGCAGCTATGGCG

TGCATTGGATTCGCCAGAGCCCGGGCAAAGGCCTGGAATGGATTGGCGTG
```

-continued
ATTTGGCGCGGCGGCAGCACCGATTATAACGCGGCGTTTATGAGCCGCGT

GACCATTAGCAAAGATAACAGCAAAAACCAGGTGAGCTTTAAACTGAGCA

GCGTGACCGCGGCGGATACCGCGGTGTATTATTGCGCGAACCATCGCGAT

TGGGGCCAGGGCACCCTGGTGACCGTGAGCAGC

Example 15: Binding of Humanized Antibody with Human PCSK9

A 96-well ELISA plate was plated, coated with 0.1 μg/ml streptavidin, and incubated at 37° C. for 60 min. Then, the solution inside the wells was discarded, and the wells were washed with washing buffer for three times. PBS solution containing 2% BSA was added for blocking for 60 minutes. After washing with washing buffer for three times, 100 μl biotin-labeled PCSK9 at 0.2 μg/ml was added to each well, incubated at 37° C. for 1 hour, and washed with washing buffer for 3 times. Then, humanized antibodies that were diluted at different dilution ratio were added, incubated at 37° C. for 1 hour. After washing with washing buffer for 3 times, HRP-labeled mouse anti-human IgG (H+L) was diluted with washing buffer at ratio of 1:10000, incubated for 1 hour at room temperature. After washing for 3 times with washing buffer, 100 μl TMB substrate solution was added for developing, and reacted for 10 minutes at room temperature. The reaction was terminated by 100 μl 12M HCl solution and the absorbance was read out at 450 nm.

Figure 12:
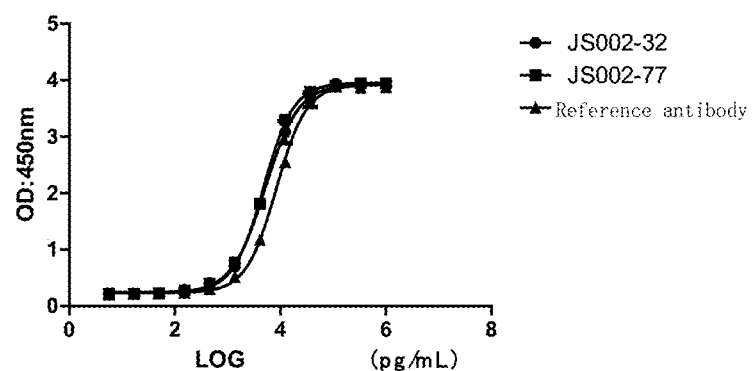
FIG. 12: Binding of humanized antibody with human PCSK9.
Figure 13:
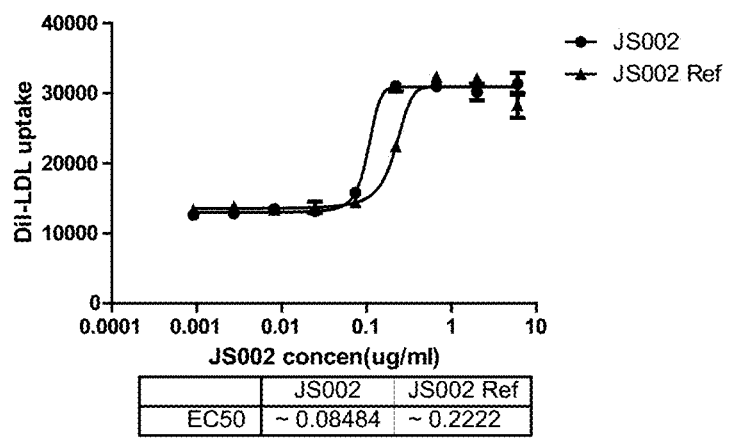
FIG. 13: Effect of humanized antibody on LDL uptake of HepG2 cells.

As shown in FIG. 12, after humanization, the binding ability to the human-derived PSK9 is not changed with an EC50 value at about 5 ng/ml.

Example 16: The Effect of Humanized Antibody on the Cell-Uptake of LDL on HepG2 Cells The humanized antibody and reference antibody(gradient diluted at different concentrations with a starting concentration at 10 μg/ml, with a 2-fold concentration gradient) and HuPCSK9-D347Y (2.5 μg/ml) were incubated at room temperature for 30 min, and added to HepG2 cells, incubated at 37° C. with 7% CO$_2$ for 1 h. Then Dil-LDL (5 μg/ml) was added, incubated at 37° C. with 7% CO$_2$ for 5 hours. After washing for 4 times with PBS, Tecan M1000 Pro was used for fluorescent detection (Ex 554 nm/Em 571 nm).

Figure 14:
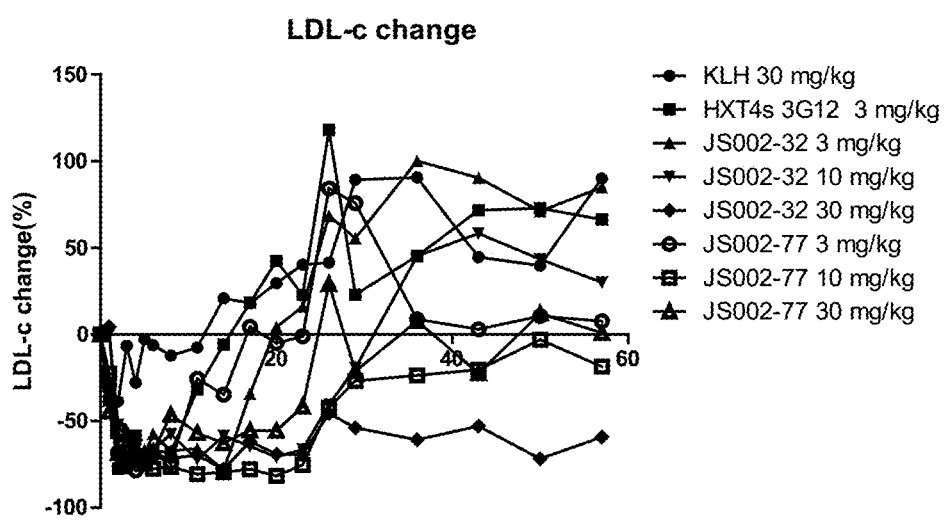
FIG. 14: Humanized antibody can effectively reduce in vivo LDL-c level in Cynomolgus monkey (*Macaca fascicularis*).

As shown in FIG. 14, the humanized antibody can effectively inhibit the binding of PCSK9 with LDLR, to improve the LDL uptake of HepG2 cells with an IC50 value of around 1 μg/ml.

Example 17: Humanized Antibody can Effectively Reduce the In Vivo LDL-c in Cynomolgus Monkey (*Macaca fascicularis*)

Cynomolgus monkey was used as an animal model with subcutaneous administration of a single dose. At different administration time point, the changes in serum LDL-c and in the antibody concentration were observed under different dosage conditions (3, 10, 30 mg/kg).

As shown in FIG. 14, through detection, it can be seen that with different administration dosages, the LDL-c amount in serum was significantly reduced. At D7 after the administration, a 70% reduction in LDL-c level was observed. Meanwhile, comparing to chimeric antibody, the half-life of humanized antibody significantly increased.

REFERENCE DOCUMENTS

Abifadel, M., et al. (2003). "Mutations in PCSK9 cause autosomal dominant hypercholesterolemia." *Nat Genet* 34(2): 154-156.

Abifadel, M., et al. (2003). "Mutations in PCSK9 cause autosomal dominant hypercholesterolemia." *Nat Genet* 34(2): 154-156.

Benjannet, S., et al. (2004). "NARC-1/PCSK9 and its natural mutants zymogen cleavage and effects on the low density lipoprotein (LDL) receptor and LDL cholesterol." *Journal of Biological Chemistry* 279(47): 48865-48875.

Fisher, T. S., et al. (2007). "Effects of pH and Low Density Lipoprotein (LDL) on PCSK9-dependent LDL Receptor Regulation." *Journal of Biological Chemistry* 282(28): 20502-20512.

Jones, S. T. and M. M. Bendig (1991). "Rapid PCR-cloning of full-length mouse immunoglobulin variable regions." *Bio/Technology* 9(1): 88-89.

Lagace, T. A., et al. (2006). "Secreted PCSK9 decreases the number of LDL receptors in hepatocytes and inlivers of parabiotic mice." *Journal of Clinical Investigation* 116 (11): 2995-3005.

Lambert, G., et al. (2009). "Molecular basis of PCSK9 function." *Atherosclerosis* 203(1): 1-7.

Seidah, N. G., et al. (2003). "The secretory proprotein convertase neural apoptosis-regulated convertase 1 (NARC-1): liver regeneration and neuronal differentiation." *Proceedings of the National Academy of Sciences* 100(3): 928-933.

Zhang, D.-W., et al. (2007). "Binding of Proprotein Convertase Subtilisin/Kexin Type 9 to Epidermal Growth Factor-like Repeat A of Low Density Lipoprotein Receptor Decreases Receptor Recycling and Increases Degradation." *Journal of Biological Chemistry* 282(25): 18602-18612.

The invention claimed is:

1. An anti-proprotein convertase subtilisin/kexin type 9 (PCSK9) antibody or an antigen-binding fragment thereof, wherein:
   the anti-PCSK9 antibody or an antigen-binding fragment thereof comprises LCDR1 consisting of the amino acid sequence of SEQ ID NO:1, LCDR2 consisting of the amino acid sequence of SEQ ID NO:2, LCDR3 consisting of the amino acid sequence of SEQ ID NO:3, HCDR1 consisting of the amino acid sequence of SEQ ID NO:4, HCDR2 consisting of the amino acid sequence of SEQ ID NO:5 and HCDR3 consisting of the amino acid sequence of SEQ ID NO:6; or
   the anti-PCSK9 antibody or an antigen-binding fragment thereof comprises LCDR1 consisting of the amino acid sequence of SEQ ID NO:7, LCDR2 consisting of the amino acid sequence of SEQ ID NO:8, LCDR3 consisting of the amino acid sequence of SEQ ID NO:9, HCDR1 consisting of the amino acid sequence of SEQ ID NO:10, HCDR2 consisting of the amino acid sequence of SEQ ID NO:11 and HCDR3 consisting of the amino acid sequence of SEQ ID NO:12; or
   the anti-PCSK9 antibody or an antigen-binding fragment thereof comprises LCDR1 consisting of the amino acid sequence of SEQ ID NO:13, LCDR2 consisting of the amino acid sequence of SEQ ID NO:14, LCDR3 consisting of the amino acid sequence of SEQ ID NO:15, HCDR1 consisting of the amino acid sequence of SEQ ID NO:16, HCDR2 consisting of the amino acid sequence of SEQ ID NO:17 and HCDR3 consisting of the amino acid sequence of SEQ ID NO:18; or
   the anti-PCSK9 antibody or an antigen-binding fragment thereof comprises LCDR1 consisting of the amino acid sequence of SEQ ID NO:19, LCDR2 consisting of the amino acid sequence of SEQ ID NO:20, LCDR3 consisting of the amino acid sequence of SEQ ID NO:21, HCDR1 consisting of the amino acid sequence of SEQ ID NO:22, HCDR2 consisting of the amino acid sequence of SEQ ID NO:23 and HCDR3 consisting of the amino acid sequence of SEQ ID NO:24; or
   the anti-PCSK9 antibody or an antigen-binding fragment thereof comprises LCDR1 consisting of the amino acid sequence of SEQ ID NO:25, LCDR2 consisting of the amino acid sequence of SEQ ID NO:26, LCDR3 consisting of the amino acid sequence of SEQ ID NO:27, HCDR1 consisting of the amino acid sequence of SEQ ID NO:28, HCDR2 consisting of the amino acid sequence of SEQ ID NO:29 and HCDR3 consisting of the amino acid sequence of SEQ ID NO:30.

2. The anti-PCSK9 antibody or an antigen-binding fragment thereof according to claim 1, comprising a heavy chain variable region with its amino acid sequence selected from the group consisting of the amino acid sequences of SEQ ID NOs: 32, 34, 36, 38, and 40, and a light chain variable region with its amino acid sequence selected from the group consisting of the amino acid sequences of SEQ ID NOs: 31, 33, 35, 37, and 39.

3. The anti-PCSK9 antibody or an antigen-binding fragment thereof according to claim 2, wherein the amino acid sequence of the heavy chain variable region is the amino acid sequence of SEQ ID NO: 32 and the amino acid sequence of the light chain variable region is the amino acid sequence of SEQ ID NO: 31, or
   the amino acid sequence of the heavy chain variable region is the amino acid sequence of SEQ ID NO: 34 and the amino acid sequence of the light chain variable region is the amino acid sequence of SEQ ID NO: 33, or
   the amino acid sequence of the heavy chain variable region is the amino acid sequence of SEQ ID NO:36 and the amino acid sequence of the light chain variable region is the amino acid sequence of SEQ ID NO:35, or
   the amino acid sequence of the heavy chain variable region is the amino acid sequence of SEQ ID NO:38 and the amino acid sequence of the light chain variable region is the amino acid sequence of SEQ ID NO: 37, or
   the amino acid sequence of the heavy chain variable region is the amino acid sequence of SEQ ID NO: 40 and the amino acid sequence of the light chain variable region is the amino acid sequence of SEQ ID NO: 39.

4. The anti-PCSK9 antibody or an antigen-binding fragment thereof according to claim 1, which is a chimeric antibody, a humanized antibody, or a fully human antibody.

5. The anti-PCSK9 antibody or an antigen-binding fragment thereof according to claim 1, wherein the anti-PCSK9 antibody comprises a heavy chain with its amino acid sequence selected from the group consisting of the amino acid sequences of SEQ ID NO:47 and SEQ ID NO:49 and a light chain with its amino acid sequence consisting of SEQ ID NO:45.

6. A pharmaceutical composition comprising the antibody or an antigen-binding fragment thereof according to claim 1 and a pharmaceutically acceptable carrier.

7. The pharmaceutical composition of claim 6 comprising an antibody comprising a heavy chain with its amino acid sequence selected from the group consisting of the amino acid sequences of SEQ ID NO:47 and SEQ ID NO:49 and a light chain with its amino acid sequence consisting of SEQ ID NO:45, or an antigen-binding fragment thereof.

8. An immunoconjugate comprising an antibody or an antigen-binding fragment thereof according to claim 1 conjugated to a therapeutic agent.

9. The immunoconjugate of claim 8, wherein the antibody comprises a heavy chain with its amino acid sequence selected from the group consisting of the amino acid sequences of SEQ ID NO:47 and SEQ ID NO:49, and a light chain with its amino acid sequence consisting of SEQ ID NO:45, or an antigen-binding fragment thereof.

10. The immunoconjugate of claim 9, wherein the therapeutic agent is a toxin, a radioisotope, a drug, or a cytotoxic agent.

11. An isolated nucleic acid molecule encoding the anti-PCSK9 antibody or an antigen-binding fragment thereof of claim 1.

12. The isolated nucleic acid molecule of claim 11, encoding an anti-PCSK9 antibody comprising a heavy chain with its amino acid sequence selected from the group consisting of the amino acid sequences of SEQ ID NO:47 and SEQ ID NO:49 and a light chain with its amino acid sequence consisting of SEQ ID NO:45, or an antigen-binding fragment thereof.

13. The isolated nucleic acid molecule of claim 12, wherein the isolated nucleic acid molecule is selected from the group consisting of SEQ ID NOS: 46, 48 and 50.

14. An expression vector comprising the isolated nucleic acid molecule according to claim 11.

15. The expression vector of claim 14 comprising a nucleic acid molecule encoding an anti-PCSK9 antibody comprising a heavy chain with its amino acid sequence selected from the group consisting of the amino acid sequences of SEQ ID NO:47 and SEQ ID NO:49 and a light chain with its amino acid sequence consisting of SEQ ID NO:45, or an antigen-binding fragment thereof.

16. The expression vector of claim 14 comprising a nucleic acid molecule selected from the group consisting of SEQ ID NOS: 46, 48 and 50.

17. An isolated host cell comprising the nucleic acid molecule according to claim 11.

18. The isolated host cell of claim 17 comprising a nucleic acid molecule encoding an anti-PCSK9 antibody comprising a heavy chain with its amino acid sequence selected from the group consisting of the amino acid sequences of SEQ ID NO:47 and SEQ ID NO:49 and a light chain with its amino acid sequence consisting of SEQ ID NO:45, or an antigen-binding fragment thereof.

19. A method for improving cellular uptake of low-density lipoprotein (LDL) or reducing LDL cholesterol (LDL-c) in a subject, comprising administering to the subject a therapeutically effective amount of the antibody or an antigen-binding fragment thereof of claim 1, a pharmaceutical composition comprising the antibody or an antigen-binding fragment thereof of claim 1, or an immunoconjugate comprising the antibody or an antigen-binding fragment thereof of claim 1 conjugated to a therapeutic agent.

20. The method of claim 19, wherein the subject has a disease selected from the group consisting of dyslipidemia, hyperlipidemia, and hypercholesterolemia.

\* \* \* \* \*